(12) United States Patent
Zhang et al.

(10) Patent No.: US 11,697,700 B2
(45) Date of Patent: Jul. 11, 2023

(54) SYNTHESIS OF A CATIONIC SURFMER AND ITS COPOLYMERS FOR ENHANCED OIL RECOVERY

(71) Applicant: SAUDI ARABIAN OIL COMPANY, Dhahran (SA)

(72) Inventors: Xuan Zhang, Beijing (CN); Ming Han, Beijing (CN); Limin Xu, Beijing (CN)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 149 days.

(21) Appl. No.: 16/935,943

(22) Filed: Jul. 22, 2020

(65) Prior Publication Data
US 2022/0025090 A1   Jan. 27, 2022

(51) Int. Cl.
| | |
|---|---|
| E21B 43/16 | (2006.01) |
| C09K 8/58 | (2006.01) |
| C08F 220/58 | (2006.01) |
| C08F 220/56 | (2006.01) |
| C07C 231/12 | (2006.01) |
| C07C 233/38 | (2006.01) |

(Continued)

(52) U.S. Cl.
CPC ........ *C08F 220/585* (2020.02); *C07C 231/12* (2013.01); *C07C 233/38* (2013.01); *C08F 220/56* (2013.01); *C09K 8/584* (2013.01); *C09K 8/588* (2013.01); *E21B 43/16* (2013.01)

(58) Field of Classification Search
None
See application file for complete search history.

(56) References Cited

U.S. PATENT DOCUMENTS 6,762,154 B2 * 7/2004 Lungwitz ................ C09K 8/68
507/131
2019/0256458 A1  8/2019 Hussain et al.

FOREIGN PATENT DOCUMENTS

| CA | 2384108 A1 | 3/2001 |
|---|---|---|
| CN | 106008255 B | 1/2019 |
| WO | 2013162902 A1 | 10/2013 |

(Continued)

OTHER PUBLICATIONS

Chu et al. "Wormlike Micelles and Solution Properties of a C-22 tailed Amidosulfobetaine Surfactant" Langmuir 2010, 26(11), 7783-7791 (Year: 2010).*

(Continued)

*Primary Examiner* — Charles R Nold
(74) *Attorney, Agent, or Firm* — Osha Bergman Watanabe & Burton LLP

(57) ABSTRACT

Provided is a quaternary ammonium surfmer, that may have the following general formula (I): $N^+—R^1R^2R^3R^4$ ($X^-$), where: $R^1$ and $R^2$ may independently be H or a $C_1$-$C_3$ alkyl, $R^3$ may be a $C_{19+}$ amidoalkyl group, $R^4$ may be a $C_3$-$C_6$ alkyl having a terminal olefin double bond group, and X may be a halogen. Further provided is a method for synthesizing the quaternary ammonium surfmer and a method for recovering hydrocarbons from a subterranean formation that may include injecting a treatment fluid comprising the quaternary ammonium surfmer into the subterranean formation.

7 Claims, 18 Drawing Sheets

(51) Int. Cl.
   C09K 8/584   (2006.01)
   C09K 8/588   (2006.01)

(56) References Cited

FOREIGN PATENT DOCUMENTS

| WO | 2014120437 A1 | 8/2014 |
|---|---|---|
| WO | 2015126418 A1 | 8/2015 |

OTHER PUBLICATIONS

Pengxiang Wang et al. "The N-allyl substituted effect on wormlike micelles and salt tolerance of a C22-tailed cationic surfactant"; Soft Matter, 2017, 13, 7425-7432 (Year: 2017).*

Chu, Zonglin and Yujun Feng, "A Facile Route towards the Preparation of Ultra-Long-Chain Amidosulfobetaine Surfactants" SYNLETT, Georg Thieme Verlag Stuttgart, No. 16, Sep. 2009, pp. 2655-2658 (4 pages).

Lu, Hongsheng et al., "An Advanced Method for the Preparation of Erucyl Dimethyl Amidopropyl Betaine and Acid Solution Properties", TS110215, Tenside Surfactants Detergents, Carl Hanser Publisher, vol. 49, No. 6, Nov. 2012 (6 pages).

Yang, Chunpeng et al., "Self-assembly properties of ultra-long-chain gemini surfactants bearing multiple amide groups with high performance in fracturing fluid application", COLSUA 21513, Colloids and Surfaces A: Physiochemical and Engineering Aspects, Mar. 2017, URL: <http://dx.doi.org/10.1016/j.colsurfa.2017.03.062> (32 pages).

Renoux, D. et al., "Aqueous solution properties of hydrophobically associating copolymers", Microemulsions, Progr Colloid Polym Sci, Steinkopff-Verlag, vol. 97, 1994, pp. 213-217 (5 pages).

Zhang, Xu Feng and Wen Hui Wu, "Novel hydrophobically associative polyacrylamide with tunable viscosity", Chinese Chemical Letters, ScienceDirect, Elsevier B.V., vol. 20, 2009, pp. 1361-1365 (5 pages).

Chu, Zonglin et al., "Wormlike Micelles and Solution Properties of a C22-Tailed Amidosulfobetaine Surfactant", Langmuir Article, American Chemical Society, vol. 26, No. 11, Apr. 2010, pp. 7783-7791 (9 pages).

International Search Report and Written Opinion of the International Searching Authority issued in corresponding International Application No. PCT/US2020/045356, dated May 12, 2021 (33 pages).

* cited by examiner

C$_{22}$DMAAB

AMPS/C$_{22}$DMAAB

R= saturated or unsaturated alkyl groups having from 22 to 28 carbon atoms

X= halides

SYNTHESIS OF A CATIONIC SURFMER AND ITS COPOLYMERS FOR ENHANCED OIL RECOVERY

BACKGROUND

The use of enhanced oil recovery (EOR) processes has greatly benefited the oil and gas industry by increasing the production of problematic and underperforming hydrocarbon bearing wells and fields. The EOR processes used in modern oil and gas operations may include, for example, chemical, hydro chemical, thermal, fluid/superfluid and microbial based processes. Chemical enhanced oil recovery (chemical EOR) increases oil recovery by increasing the efficacy of water injected into the reservoir to displace the crude oil contained therein. In particular, chemical EOR can use surfactants to reduce the interfacial tension (IFT) between injection water and the crude oil, thereby releasing trapped oil in the reservoir matrix. Chemical EOR can also use polymers to increase the viscosity of injection water that controls the oil/water mobility ratio, thereby increasing the sweep efficiency of injection water.

Many carbonate reservoirs have high reservoir temperature and high brine salinity. Unfortunately, many commercial surfactants and polymers are limited or unsuitable for use for EOR applications in such reservoir conditions due to poor temperature resistance and salts tolerance.

In general, surfactants with large hydrophobes are not salinity tolerant due to the increased polarity in the brine. For example, surfactants used in oil reservoirs with long hydrophobic hydrocarbon tails are known to not be as salinity tolerant compared to surfactants with shorter hydrocarbon tails. This is partly due to an increased polarity of longer hydrophobic hydrocarbon tails in a saline, brine solution. A surfactant with a longer hydrophobic hydrocarbon tail will generally exhibit lower optimum salinity than one with a shorter tail and thus are generally considered to have limited use in chemical EOR.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments herein are directed toward a quaternary ammonium surfmer. The quaternary ammonium surfmer may have the following general formula (I): $N^+$—$R^1R^2R^3R^4$ ($X^-$), where: $R^1$ and $R^2$ are independently H or a $C_1$-$C_3$ alkyl, $R^3$ is a $C_{19+}$ amidoalkyl group, $R^4$ is a $C_3$-$C_6$ alkyl having a terminal olefin double bond group, and X is a halogen.

In another aspect, embodiments herein are directed toward a method for synthesizing a quaternary ammonium surfmer. The method may include mixing reactants including N,N-dimethyl-erucyl-1,3-propylenediamine and allyl bromide in a solvent to form a mixture, heating the mixture to a reaction temperature in a range from 30° C. to 80° C., and reacting the reactants at the reaction temperature for a time period in the range from 1 to 48 hours to form a reaction product mixture comprising the quaternary ammonium surfmer. The quaternary ammonium surfmer may then be recovered.

In another aspect, embodiments herein are directed toward a method for synthesizing a surfmer copolymer. The method may include forming a reaction mixture comprising a free radical initiator, the quaternary ammonium surfmer with one or more comonomers selected from the group consisting of acrylamide (AM), hydrolyzed acrylamide (AANa), and 2-acrylamido-2-methyl-1-propanesulfonic acid or sodium salt (AMPS). The method may further include heating the reaction mixture to a reaction temperature of 20° C. to 40° C., and reacting the quaternary ammonium surfmer with the one or more comonomers for a reaction time of 0.5 to 24 hours at a pH from 1 to 11, wherein the comonomer concentration is 5% to 40% by weight of the total solution.

In another aspect, embodiments herein relate to a method for recovering hydrocarbons from a subterranean formation comprises. The method may include injecting a treatment fluid comprising the quaternary ammonium surfmer into the subterranean formation.

Other aspects and advantages of the claimed subject matter will be apparent from the following description and the appended claims.

DETAILED DESCRIPTION

Figure 1:
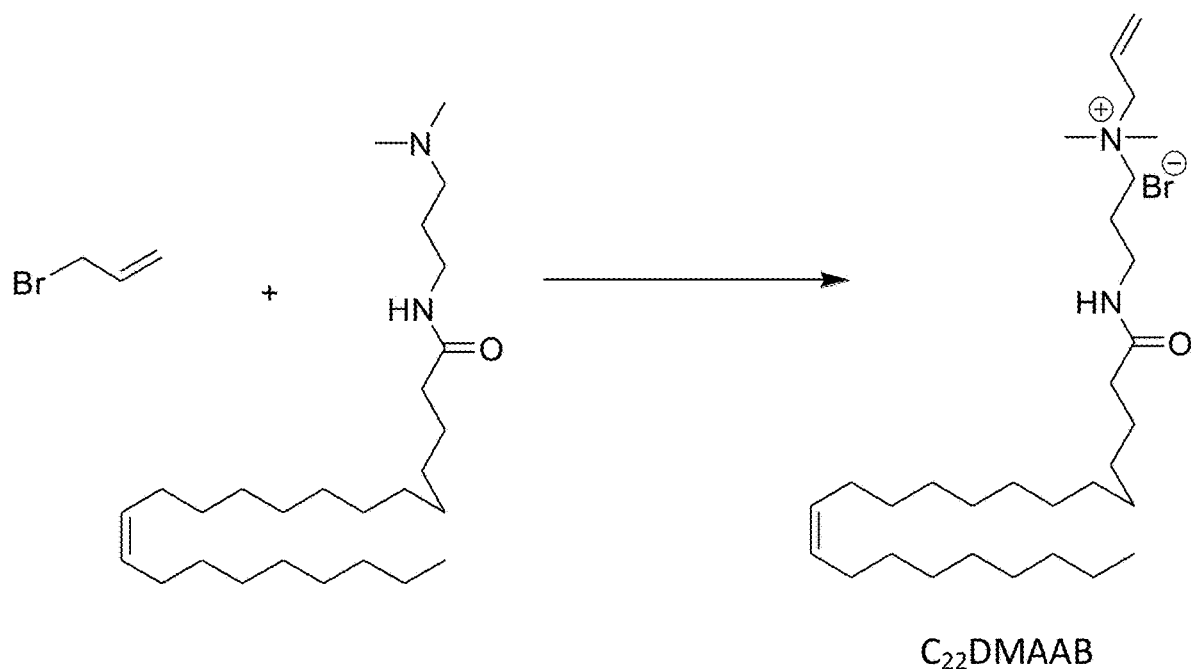
FIG. 1 illustrates a reaction scheme for the synthesis of a surfmer, $C_{22}$DMAAB, according to embodiments herein.

Embodiments herein are directed toward surfmers and surfmer copolymers, where the surfmer may include a long tail. One or more embodiments are also directed toward synthesis of the surfmers and surfmer copolymers, as well as the use of such surfmers and surfmer copolymers in chemical enhanced oil recovery (chemical EOR). One or more embodiments herein are directed toward surfmers and surfmer copolymers that may exhibit tolerance to high temperature and/or high salinity conditions. A surfmer, also known as a reactive surfactant, a polymerizable surfactant, or a surface active monomer, has properties including interfacial tension (IFT) reduction as a surfactant, and the ability to polymerize as a monomer. The surfmer and surfmer copolymers disclosed herein may have a long hydrophobic tail (>18 carbon atoms) and have an ability to be used advantageously in carbonate reservoirs where other surfactants and chemical EOR methods are inapplicable.

Surfmers according to embodiments herein, described further below, may have a long hydrophobic tail, such as a long alkyl chain having greater than 18 carbon atoms, greater than 20 carbon atoms, or greater than 22 carbon atoms, such as 19 to 28 carbon atoms. The alkyl chain may be saturated or unsaturated. The hydrophilic head group may include a nitrogen salt or a nitrogen cation, where the nitrogen salt or cation may include a polymerizable vinyl substituent group. The long alkyl chain and hydrophilic head group may provide the surfactant functionality, and the polymerizable vinyl group may provide the monomeric functionality of the surfmer.

One or more embodiments of the present disclosure relate to the synthesis of a surfmer composed of a quaternary ammonium salt with an olefin double bond in its head group. In one or more embodiments, the surfmer is a monomer and may be used to form copolymers; both the surfmer and the surfmer copolymers may be synthesized, as described below, and further may be used in chemical EOR to improve recovery of oil from high salinity and/or high temperature reservoirs.

Surfmers according to embodiments herein, for example, may be polymerized with other comonomers and with each other under conditions as-designed for the respective reaction components, such as acrylamide-containing comonomers, as described further below. In one or more embodiments, the surfmers may be co-polymerized in a free-radical aqueous phase reaction with an olefin double bond of an acrylamide or acrylamide derivative.

When a surfmer has, or a surfmer copolymer contains surfmer monomers having, tail lengths of 18 carbon atoms or less, a high surfmer content in the overall copolymer may provide for synthetic products that have relatively lower molecular weight, short polymer chains with a high synthetic cost. Using surfmer monomers having tail lengths of 18 carbons or less but with a low surfmer monomer content in the overall polymer, however, may lead to reduced performance in viscous solution and lower salt tolerance when compared to a copolymer with high surfmer monomer content. Embodiments herein have been found to overcome such shortcomings of surfmers having shorter tails.

In one or more embodiments, surfmer copolymers disclosed herein may be configured to have a small concentration of long chain surfmer monomers, allowing for EOR performance in viscous, high temperature, and high salinity solutions. In one or more embodiments, the range of surfmer concentration in the copolymer may be from 0.01 mole percent (mol %) to 0.5 mol %. In some embodiments, the copolymer may have a molecular weight in a range from 1 megadalton (MDa) to 9 MDa. These surfmer copolymers may also exhibit long-term stability. The stability of surfmers and surfmer copolymers herein allow such compounds to be advantageously used during chemical EOR.

During chemical EOR, an ultra-low IFT may be achieved by addition of a surfmer or a surfmer copolymer according to embodiments herein downhole, and may mobilize residual oil trapped in a reservoir. As the surfactant used downhole must have properties to withstand harsh reservoir conditions, including high salinity, surfmers and surfmer copolymers according to embodiments herein are more suitable than many commercially available surfactants for EOR use, where the high temperature and/or high salinity may exclude those that have properties of poor temperature resistance and/or low salt tolerance.

In one or more embodiments, the surfmer and surfmer copolymers may be used as surfactants that reduce interfacial tension in harsh reservoir conditions for EOR application in carbonate reservoirs, which are known to have high temperature and/or high salinity conditions. "Harsh reservoir conditions," as used herein, may refer to brines or seawater with salinity of 57,670 ppm or greater, at reservoir temperatures of around 95° C. or greater.

Surfmer compositions according to embodiments herein may include quaternary ammonium salts that are coordinated to, for example, a halogen anion of fluoride, chloride, bromide, or iodide. In one or more embodiments, the quaternary ammonium ion or salt may have the general formula $N^+R^1R^2R^3R^4$.

Two of the R groups, $R^1$ and $R^2$, may independently be an H atom or a $C_1$-$C_3$ alkyl group. In one or more embodiments, one of the two alkyl $R^1$ and $R^2$ groups is a methyl, an ethyl, or a propyl. In other embodiments, $R^1$ and $R^2$ are both the same, such as both being an H atom or a $C_1$-$C_3$ alkyl group; in other embodiments, $R^1$ and $R^2$ are both methyl groups.

$R^3$ may be an amidoalkyl group having greater than 18 carbons. For example, the amidoalkyl group may include 19 or more carbon atoms, such as 22 to 32 carbon atoms. In some embodiments, the amidoalkyl group may include a $C_2$-$C_4$ alkyl group bridging from the nitrogen cation to the amido group. The amido alkyl group may also include a $C_{22+}$ alkyl group as the large hydrophobic tail, such as a $C_{22}$ to $C_{28}$ alkyl group, where the alkyl group may be saturated or unsaturated. In one or more embodiments, the alkyl group may be a $C_{22}$ to $C_{28}$ unsaturated alkyl group, and in some embodiments may include an internal (non-terminal) vinyl group. In one or more embodiments, the $R^3$ group may be an erucyl amidoalkyl or an erucyl amidopropyl group.

In one or more embodiments, $R^4$ may be an olefinic $C_3$-$C_6$ alkyl group, such as a $C_3$-$C_6$ alkyl having a terminal a vinyl group. In other embodiments, $R^4$ is an allyl or a 1-butene group. In general, embodiments of surfmers herein include a relatively polar head group (an amidoalkyl quaternary ammonium salt, for example) that includes a reactive terminal olefin group at $R^4$. $R^4$ should be a relatively small hydrocarbon chain so as to not detract from the surfactant ability of the surfmer, but should include a reactive terminal olefin group, providing the monomeric function of the surfmer.

In some embodiments the surfmer composition may be a quaternary ammonium salt with the following general formula: $R^5$—CH=CH—$R^6$—COHN—$R^7$—$N^+R^1R^2R^4$ ($Br^-$). The $R^1$, $R^2$, and $R^4$ groups may be as described above. $R^5$ and $R^6$ may be positioned cis- or trans-relative to the internal CH=CH group, and in particular embodiments may be the cis isomer.

In one or more embodiments, the $R^5$ group may be a straight chain or branched $C_8$-$C_{16}$ alkyl group, such as a $C_8$-$C_{12}$ straight chain alkyl group. In other embodiments, $R^5$ may be a $C_8$ alkyl group.

In one or more embodiments, the $R^6$ group may be a straight chain or branched $C_9$-$C_{16}$ alkyl group, such as a $C_9$-$C_{12}$ alkyl group. In other embodiments, $R^6$ may be a $C_{11}$ alkyl group.

In one or more embodiments, $R^7$ may be a $C_2$-$C_6$ alkyl group, such as an ethyl, propyl, or a butyl group. In other embodiments, $R^7$ may be a propyl group.

In one or more embodiments, the quaternary ammonium surfmer herein is a reaction product of N,N-dimethyl-erucyl-1,3-propylenediamine and allyl bromide, termed herein as erucyl amidopropyl dimethyl allyl ammonium bromide ("$C_{22}$DMAAB"), which may have the structure as shown below.

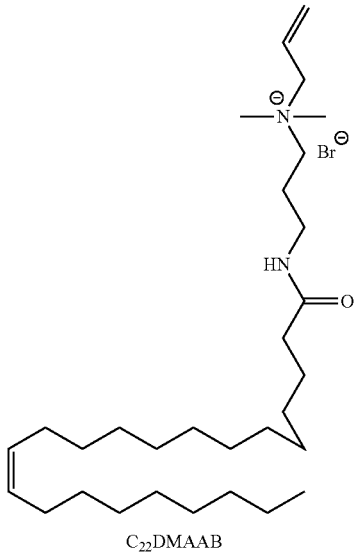

$C_{22}$DMAAB

In one or more embodiments, surfmers as described above may be synthesized via reaction of a diamine and an alkyl halide compound having a terminal olefinic group. Diamines useful in synthesizing the surfmers according to embodiments herein may include amine compounds of the general formula $NR^1R^2R^3$, where $R^1$, $R^2$, and $R^3$ are as described above. In some embodiments, the diamine may be N,N-dimethyl-erucyl-1,3-propylene diamine. Alkyl halides useful in embodiments herein may include $C_3$-$C_6$ alkyl halides with a terminal olefin double bond, X—$R^4$, where X may be fluoride, bromide, iodide, or chloride, and $R^4$ may be as described above, having a reactive terminal olefin, such as an allyl group or a 1-butene group. In some embodiments, the alkyl halide may be allyl bromide. In one or more embodiments, the alkyl halide is a primary alkyl halide.

Reaction of the diamine and the alkyl halide may be conducted, for example, by initially dissolving or suspending the reactants in an appropriate solvent. Solvents useful in embodiments herein may include alcohol and water mixtures including methanol/water, ethanol/water, propanol/water, and isopropanol/water. In some embodiments, the solvent may have an alcohol to water volume ratio ranging from 1:10 to 10:1. Reaction conditions selected may be suitable for second-order nucleophilic substitutions.

The reaction of the diamine and alkyl halide may be conducted, for example, at a temperature in the range from about 30° C. to about 80° C. In some embodiments, the reaction of the diamine and the alkyl halide may be conducted at a temperature in a range from about 50° C. to about 70° C., such as at a temperature of about 60° C. In general, the reaction temperature chosen may be appropriate for reflux with the solvent used.

The reaction may be conducted over a time period in a range from about 1 hour to about 48 hours. For example, in some embodiments, the reaction may be conducted over a time period in a range from about 5 hours to about 24 hours.

As a specific example, a surfmer of erucyl amidopropyl dimethyl allyl ammonium bromide, $C_{22}$DMAAB, may be synthesized through the interaction between N,N-dimethyl-erucyl-1,3-propylenediamine and allyl bromide. FIG. 1 outlines the synthesis route of $C_{22}$DMAAB, further described in the Examples below. The reaction of N, N-dimethyl-erucyl-1,3-propylenediamine and allyl bromide in ethanol as solvent may be conducted at a temperature in the range from about 30° C. to 80° C., such as about 60° C., for 1 hour to 48 hours. In one or more embodiments, methanol or organic solvents such as t-butanol, glycol, or a polyoxyalkylene may be used. In one or more embodiments, the reaction is complete in about 5 hours to 24 hours at 50° C. to 70° C. Reaction progress may be monitored by any suitable means known in the art, including, for example, monitoring disappearance of starting material by various forms of qualitative or quantitative chromatography, spectrometry, or spectroscopy.

When the reaction is complete, the solvent may be removed under reduced pressure. One or more optional washing steps may be used, if desired. The crude reaction product may then be recrystallized, and as an example, acetone may be used as the recrystallization solvent. The recrystallized product may be cooled, such as at a temperature of 0° C. to 15° C., such as at 5° C., for 5 hours to 48 hours. Following recrystallization and cooling, and as a specific example, $C_{22}$DMAAB may be recovered as a light yellow viscous product.

Surfmers according to one or more embodiments herein, such as $C_{22}$DMAAB and other embodiments envisioned, for example, may have a very low or ultra-low IFT. As used herein, very low or ultra-low refers to IFT having a magnitude of $10^4$ to $10^{-3}$ millinewton per meter (mN/m) or lower.

In one or more embodiments, the quaternary ammonium salt surfmers are stable for their intended use and resist elimination reactions, not limited to mild Hoffmann elimination reactions.

Surfmers according to one or more embodiments herein may have a very low or ultra-low IFT, even when measured in seawater having a high salinity. As used herein, a high salinity refers to brines or fluids having a salt concentration greater than 50,000 ppm, greater than 51,000 ppm, greater than 52,000 ppm, greater than 53,000 ppm, greater than 54,000 ppm, greater than 55,000 ppm, greater than 56,000 ppm, greater than 57,000 ppm, or greater than 57,669 ppm. A very high salinity refers to a salt or brine concentration of greater than or equal to 100,000 ppm (or milligram per liter, mg/L) total dissolved salts.

The very low IFT values may be achieved at a high temperature as may be encountered in a reservoir, such as at temperatures of 90° C. or greater, or 95° C. or greater. In one or more embodiments, the upper temperature limit for use of surfmers herein is estimated to be about 120° C. The combination of these properties (temperature resistance, salinity resistance, stability, very low IFT) render the $C_{22}DMAAB$ and other surfmers and surfmer copolymers according to embodiments herein suitable for use as chemical EOR agents, including in harsh reservoir conditions. Surfmers according to embodiments herein may be sufficiently surface active to produce an effect of imbibition on a rock surface, while lowering IFT to an effective degree between oil and water for imbibition.

Surfmer Copolymers

The above-described surfmers may be used to form copolymers according to embodiments herein. As an example, the quaternary ammonium surfmers may be reacted to form a copolymer with acrylamide (AM) or acrylamide derivatives via free radical polymerization. The free radical polymerization may be conducted, for example, in an aqueous environment using a free radical initiator.

Comonomers useful in embodiments herein may include acrylamide, methacrylamide, ethylacrylamide, propylacrylamide, isopropylacrylamide, tert-butyl acrylamide, as well as derivatives of such compounds. In some embodiments, for example, the acrylamide monomer may include 2-acrylamido-2-methyl-1-propane sulfonic acid (AMPS)

In various embodiments, the conditions for the aqueous radical polymerizations may include a reaction temperature in the range from about 10° C. to about 40° C., where the reaction temperature selected may be based upon the particular comonomer and initiator(s) being used In one or more embodiments, surfmer monomers described above may be copolymerized with 2-acrylamido-2-methyl-1-propane sulfonic acid (AMPS) to form a copolymer. For example, in some embodiments, $C_{22}DMAAB$ may be copolymerized with AMPS to form the copolymer surfmer AMPS/$C_{22}DMAAB$, illustrated below:

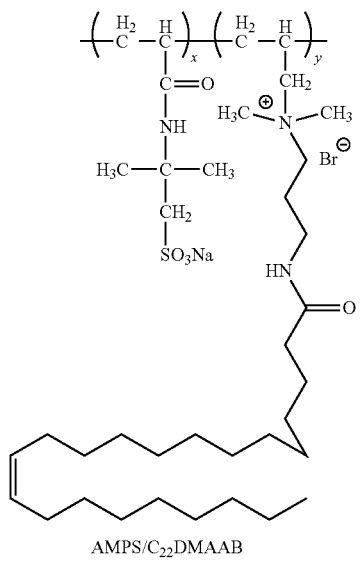

Figure 2:
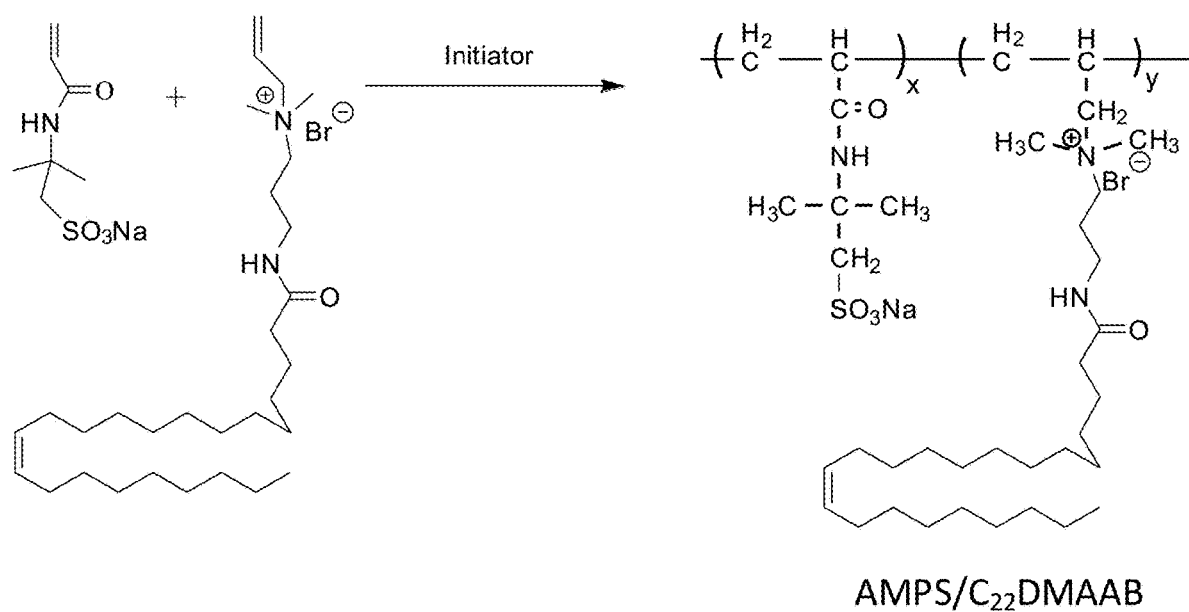
FIG. 2 illustrates a reaction scheme for the synthesis of a surfmer copolymer, AMPS/$C_{22}$DMAAB, according to one or more embodiments herein.

AMPS/$C_{22}DMAAB$ where x and y are greater than zero. In some embodiments, the surfmer copolymer may have the comonomers present at a mole ratio x:y in the range from 200:1 to 4000:1. In other embodiments, the surfmer copolymer may have the comonomer present at a mole ratio x:y in the range from 100:0.02 to 100:0.5. In further embodiments, the commoner is present at a mole ratio x:y in the range such as 100:0.03 to 100:0.4, from 100:0.04 to 100:0.3, or from 100:0.05 to 100:0.25. A reaction scheme for the synthesis of AMPS/$C_{22}DMAAB$ is depicted in FIG. 2. While $C_{22}DMAAB$ is illustrated, copolymers with other surfmers according to embodiments herein is also envisioned. In one or more embodiments, the copolymer may have a molecular weight in a range from about 1 MDa to 9 MDa.

In other embodiments, the above-described surfmers, such as $C_{22}DMAAB$, may be copolymerized with AM to form a copolymer surfmer, such as illustrated below.

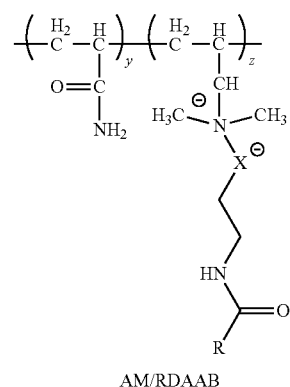

AM/RDAAB where y and z are greater than zero. In some embodiments, the surfmer copolymer may have the comonomers present at a ratio y:z in the range from 200:1 to 4000:1. In other embodiments, the surfmer copolymer may have the comonomer present at a mole ratio y:z in the range from 100:0.02 to 100:0.5. In further embodiments, the commoner is present at a mole ratio x:y in the range such as 100:0.03 to 100:0.4, from 100:0.04 to 100:0.3, or from 100:0.05 to 100:0.25. In some embodiments, such as where R is an erucyl group, the copolymer formed may be AM/$C_{22}DMAAB$. In one or more embodiments, the copolymer may have a molecular weight in a range from about 1 MDa to 7 MDa.

Figure 3:
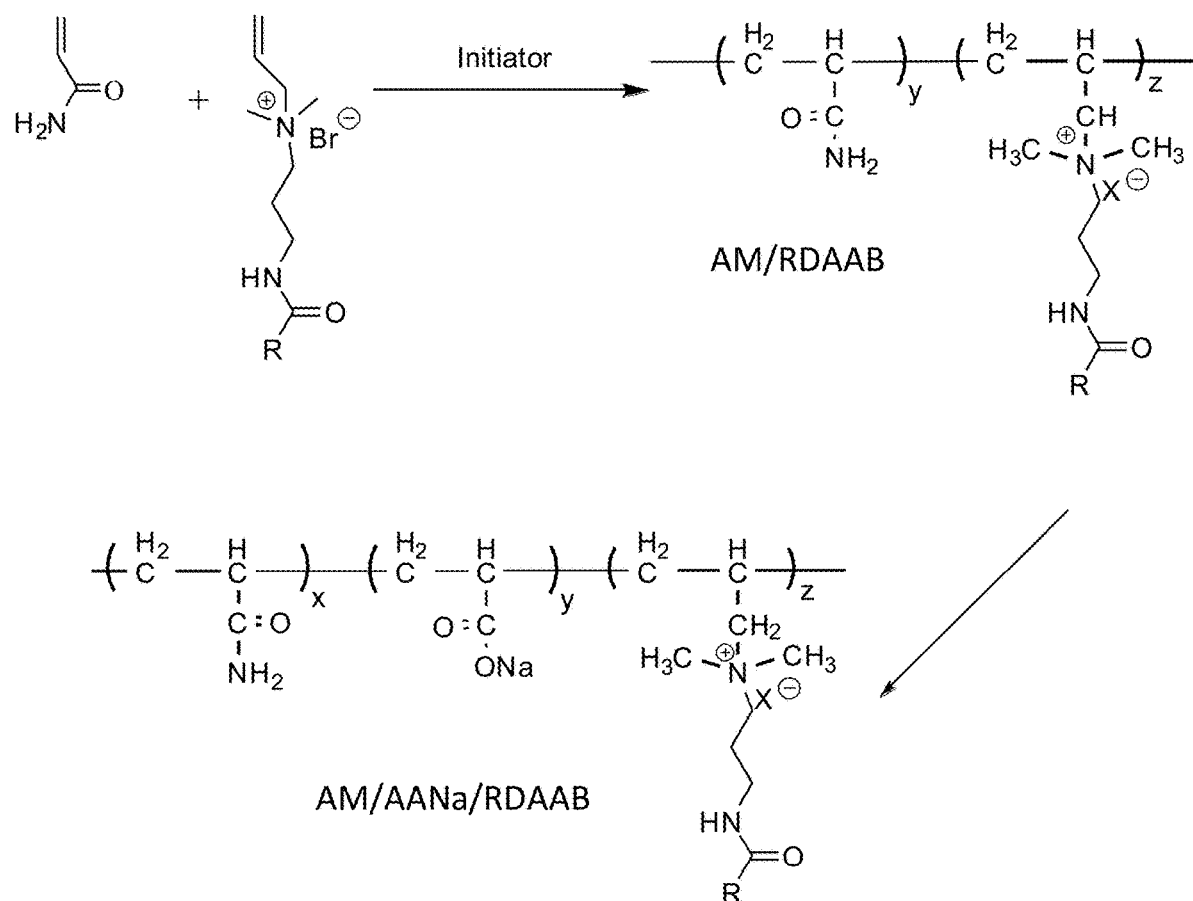
FIG. 3 illustrates a reaction scheme for the synthesis of a surfmer copolymer, AM/AANa/$C_{22}$DMAAB, according to one or more embodiments herein.

In some embodiments, the surfmer copolymers may be partially hydrolyzed to form terpolymers. The hydrolysis may be performed, for example, using inorganic alkaline compounds, such as sodium hydroxide, and may target the amine group of the acrylamide comonomer. Hydrolysis may be conducted, for example, at reaction temperature in the range of 40° C. to 120° C., such as in the range from 60° C. to 100° C., over a time period of 0.5 to 6 hours. Copolymers herein may be reacted to a degree of hydrolysis in the range from 1 to 60 mole percent, such as 5 to 40 mole percent. For example, a copolymer surfmer such as AM/$C_{22}DMAAB$ may be partially hydrolyzed to form AM/AANa/$C_{22}DMAAB$, depicted below. A reaction scheme to form AM/RDMAAB and the hydrolyzed form AM/AANa/RDAAB is illustrated in FIG. 3.

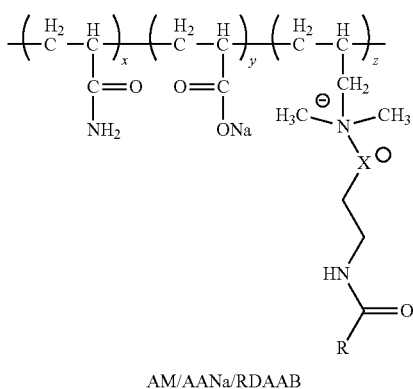

AM/AANa/RDAAB where x, y, and z are each greater than zero. In some embodiments, the hydrolyzed surfmer copolymer may have the monomeric units present at a ratio (x+y):z in the range from 200:1 to 4000:1. In other embodiments, the surfmer copolymer may have the comonomer present at a mole ratio (x+y):z in the range from 100:0.02 to 100:0.5, such as in 100:0.03 to 100:0.4, from 100:0.04 to 100:0.3, or from 100:0.05 to 100:0.25. A ratio of x:y will depend upon the degree of hydrolysis, which, as noted above, may be in the range from 5 to 40 mol % in some embodiments. Accordingly, a ratio of x:y may be in a range from 95:5 to 60:40, for example.

Surfmer copolymers herein may be configured to have a small concentration of long chain surfmer monomers, such as from a lower limit of 0.01 mol %, 0.05 mol %, 0.08 mol %, or 0.10 mol % to an upper limit of 1 mol %, 0.5 mol % or 0.15 mol %, where any lower limit may be combined with any upper limit. The low surfmer content may provide for chemical EOR performance in viscous, high temperature, and high salinity solutions. These surfmer copolymers may also exhibit long-term stability. The stability of surfmers and surfmer copolymers herein allow such compounds to be advantageously used during chemical EOR.

The above-described surfmer copolymers may be formed, for example, by free radical polymerization. The reactive head group of the surfmer, including a terminal vinyl group, may be reacted with vinyl groups of the acrylamide compounds to form a copolymer.

Synthesis of surfmer copolymers can be initiated by a free radical initiator in aqueous solution to form high molecular weight copolymers. One or more embodiments of synthetic routes are depicted in FIGS. 2 and 3.

In one or more embodiments, the comonomers that may be used include acrylamide and acrylamide derivatives. Other non-limiting examples of comonomers include 2-acrylamido-2-methyl-1-propane sulfonic acid (AMPS), acrylamide (AM), and hydrolyzed acrylamide (AANa).

Initiators that may be used to initiate the copolymerization reaction may include any aqueous stable free radical initiator. Mixtures of initiators may also be used. Examples of such initiators may include 2,2-azobis[2-(2-imidazolin-2-yl)propane]dihydrochloride (AIBI), potassium persulfate (KPS), sodium bisulfite (NaHSO$_3$), and combinations thereof, among numerous others as known in the art, including 2,2'-azobis[2-methylpropionamidine]dihydrochloride (AIBA).

In addition to the few surfmer copolymers described above, other surfmer copolymers comprising one or more embodiments of surfmers presented herein can be copolymerized with an acrylamide or acrylamide derivatives to form various additional surfmer copolymers.

The copolymerization of AMPS and C$_{22}$DMAAB are used to synthesize AMPS/C$_{22}$DMAAB, for example. AM and C$_{22}$DMAAB are used to synthesize copolymer AM/C$_{22}$DMAAB, for example. AM/AANa/C$_{22}$DMAAB is synthesized by partial hydrolysis of AM/C$_{22}$DMAAB, for example. Beyond the listed few surfmer copolymers above, others comprising one or more embodiments of surfmers presented herein can be polymerized with an acrylamide or acrylamide derivative to form various surfmer copolymers.

The copolymerization of comonomer with the comonomer surfmer begins with a free-radical initiation. During the polymerization synthesis, a free radical reaction proceeds from attachment of an olefin double bond of one or more comonomer to an olefin double bond of one or more surfmer (comonomer surfmer). The free radical polymerization proceeds by way of known reaction mechanisms. Control of chain growth and termination of free radical polymerization may also be conducted. Termination procedures include but are not limited to introduction of a termination agent, increase/decrease in concentration of a starting reagent or solvent, light or temperature control, and various other known methods of termination.

A post polymerization functionalization may be conducted in one or more embodiments after the polymerization. In one instance, a post polymerization functionalization is a hydrolysis process to form a three component copolymer of AM/AANa/C$_{22}$DMAAB. FIG. 3 shows one or more embodiments of synthetic route of the copolymer AM/AANa/C$_{22}$DMAAB. As presented above, a three component copolymer, not limited to AM/AANa/C$_{22}$DMAAB, can also be formed by adding three comonomers together during the polymerization process.

Enhanced Oil Recovery Using Surfmer and Surfmer Copolymers

In one or more embodiments, the synthesized surfmers are used for application in EOR for carbonate reservoirs. These can be used either as an individual surfmer monomer, a copolymer variation, or both simultaneously. In particular, embodiments of the present disclosure may involve injection of a treatment fluid containing a surfmer monomer, a surfmer copolymer, surfmer copolymer derivative, or mixtures thereof into a formation, specifically, a reservoir section under high temperature and high salinity environments. The surfmer, surfmer copolymer, surfmer copolymer derivative, or mixtures thereof may be present in the treatment fluid in an amount ranging from 20 mg/L to 5000 mg/L. In one or more embodiments, the concentration of surfmer as surfactant is from 50 mg/L to 2000 mg/L. In one or more other embodiments, the concentration of copolymer is from 2000 mg/L to 5000 mg/L.

In at least one embodiment, the treatment fluids of the present disclosure can be used in a secondary oil recovery process in carbonate reservoirs. In at least one embodiment, the treatment fluids can be used in a tertiary oil recovery process. In at least one embodiment, the treatment fluids can be used in both a secondary oil recovery process and a tertiary oil recovery process. Secondary oil recovery processes can be implemented in a green field after depletion of natural pressure support. Tertiary oil recovery process can be applied in matured oil fields after secondary oil recovery processes. Because the treatment fluids are aqueous based, the treatments can be used in both types of oil recovery processes.

It is envisioned that treatment fluids of the present disclosure containing the surfmers, surfmer copolymers, and surfmer copolymer derivatives described herein may be used as one of or in several sequential injections, some of which or all of which may optionally contain the surfmers, surfmer copolymers, and surfmer copolymer derivatives. For example, in a first injection, a slug of a treatment fluid may be pumped through an injection well, the total volume of the slug injected through the injection well is between 0.01 pore volumes (PV) and 0.1 PV. In the first injection, the amount of surfmer, surfmer copolymer, or surfmer copolymer derivative may optionally be in the range between 0.05 wt. % and 0.5 wt. % of the total volume. The treatment fluid in the first injection can pre-treat the reservoir to create a favorable environment for the treatment fluid to act in oil recovery by mitigating the adverse effects due to the salinity of the formation water in the reservoir. As a result of these functions, the first injection prepares the reservoir for the second injection. The first injection is followed by a second injection.

In a second injection, a slug of treatment fluid is injected through the injection well at a total volume of the slug between 0.1 PV and 0.5 PV. The treatment fluid in the second injection can free the oil present in the pores of the rock formation to produce a mobilized oil, improving the microscopic sweep efficiency. The second injection is followed by a third injection.

In the third injection, a slug of treatment fluid is injected through the injection well at a total volume of between 0.3 PV and 1.0 PV. The third injection can enhance the contact between the fluids and the reservoir, improving macroscopic sweep efficiency. In addition, the third injection maintains the benefit on the microscopic sweep efficiency due to the second injection. The third injection is followed by a fourth injection.

The fourth injection may include a slug of treatment fluid with a total volume injected through the injection well in the range of between 1.0 PV and 2.0 PV. The fourth injection can maintain the integrity of the slugs, which can maintain the effect of the treatment fluid in wettability alteration. Additionally, the fourth injection can act as a buffer between a chase seawater and the treatment fluid of the third injection.

While the mobilized oil is primarily freed during interaction between the treatment fluid and the in-situ rock during the second injection, each of the first injection through fourth injections may contribute to the production of mobilized oil, the oil freed from the pores of the in-situ rock.

Upon injection, the surfmers and copolymers thereof may interact favorably with in-situ rock of and fluids present in the reservoir (such as a carbonate reservoir) to alter wettability and improve microscopic sweep efficiency, resulting in increased release of oil from the pores in the in-situ rock.

Finally, a chase seawater, having a salinity greater than 35,000 wt. ppm (weight parts per million), for example, may be injected to drive the four injections slugs through the formation. As each of the slugs of each injection move through the formation it interacts with the in-situ rock continuing to produce amounts of mobilized oil. The mobilized oil is pushed by the injections toward the production well. In at least one embodiment, the chase seawater injection continues until the production of the mobilized oil from the production well is negligible.

The surfmer $C_{22}DMAAB$ performs well under harsh conditions including high temperature and high salinity environments. The copolymers synthesized from $C_{22}DMAAB$ also exhibit good performance with temperature and saline resistance.

Synthetic surfmers and copolymers disclosed herein operate at high temperatures above 90° C. and are shown to have good thermal stability and surfactant properties at 95° C. These synthetic molecules also perform well at high salinity conditions at 60,000 ppm of salt and higher.

EXAMPLES

Example 1A: Synthesis of $C_{22}DMAAB$ 21.14 grams (g) (or 50 millimole, mmol) N,N-dimethylerucyl-1,3-propylenediamine and 6.65 g (or 55 mmol) allyl bromide were dissolved in 100 milliliter (mL) ethanol. Then, the mixture was stirred at 60° C. for 24 hours. After the reaction was complete, the ethanol was removed under reduced pressure. The crude product was recrystallized from acetone and transferred into a refrigerator at 0-5° C. for 48 hours. A light yellow viscous product was obtained by filtration of the solution and the yield of the product surfmer $C_{22}DMAAB$ was 73.7%. The molecular weight of the product compound is approximately 543.74 gram per mole (g/mol) according to the chemical structure.

Characterization of $C_{22}DMAAB$

Figure 4:
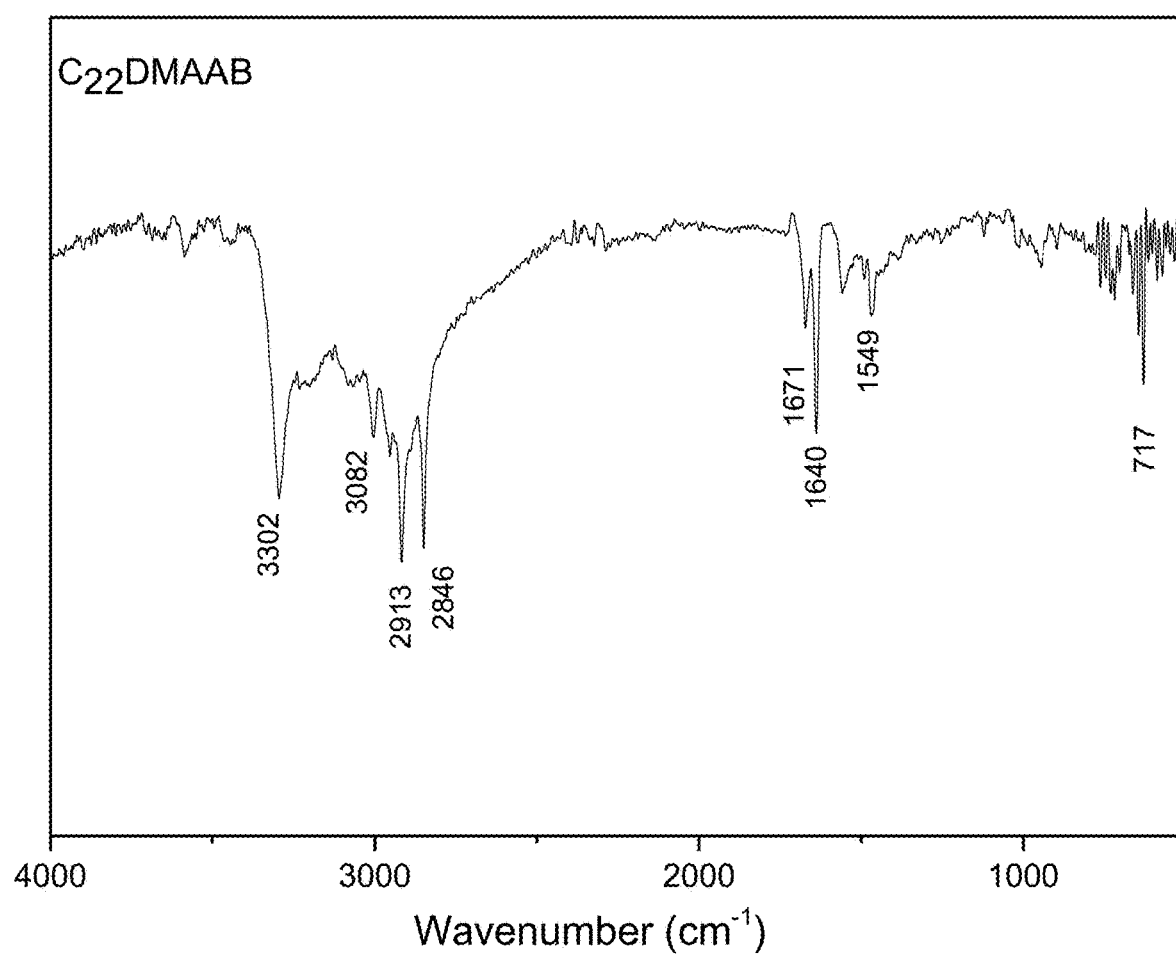
FIG. 4. is an IR spectrum of a surfmer, $C_{22}$DMAAB, according to one or more embodiments herein.

The infrared (IR) spectrum of $C_{22}DMAAB$ was taken and is displayed in FIG. 4. IR spectroscopy results include the following wavenumber ($cm^{-1}$) peaks: 3302 $cm^{-1}$, 3082 $cm^{-1}$, 2913 $cm^{-1}$, 2846 $cm^{-1}$, 1671 $cm^{-1}$, 1640 $cm^{-1}$, 1549 $cm^{-1}$, and 717 $cm^{-1}$. Characteristically, a wide absorption at 3302 $cm^{-1}$ may be due to the —N—H stretching vibration. The peaks at 2913 $cm^{-1}$ and 2846 $cm^{-1}$ are considered stretching vibrations of —$CH_3$ and —C—H (—$CH_2$—) groups. The peak at 1671 $cm^{-1}$ may be the —C═O stretching vibration. The peaks at 3082 $cm^{-1}$ and 1640 $cm^{-1}$ may represent the carbon double bond. The peak at 717 $cm^{-1}$ may indicate the alky chain.

Critical Micellar Concentration of $C_{22}DMAAB$

Figure 5:
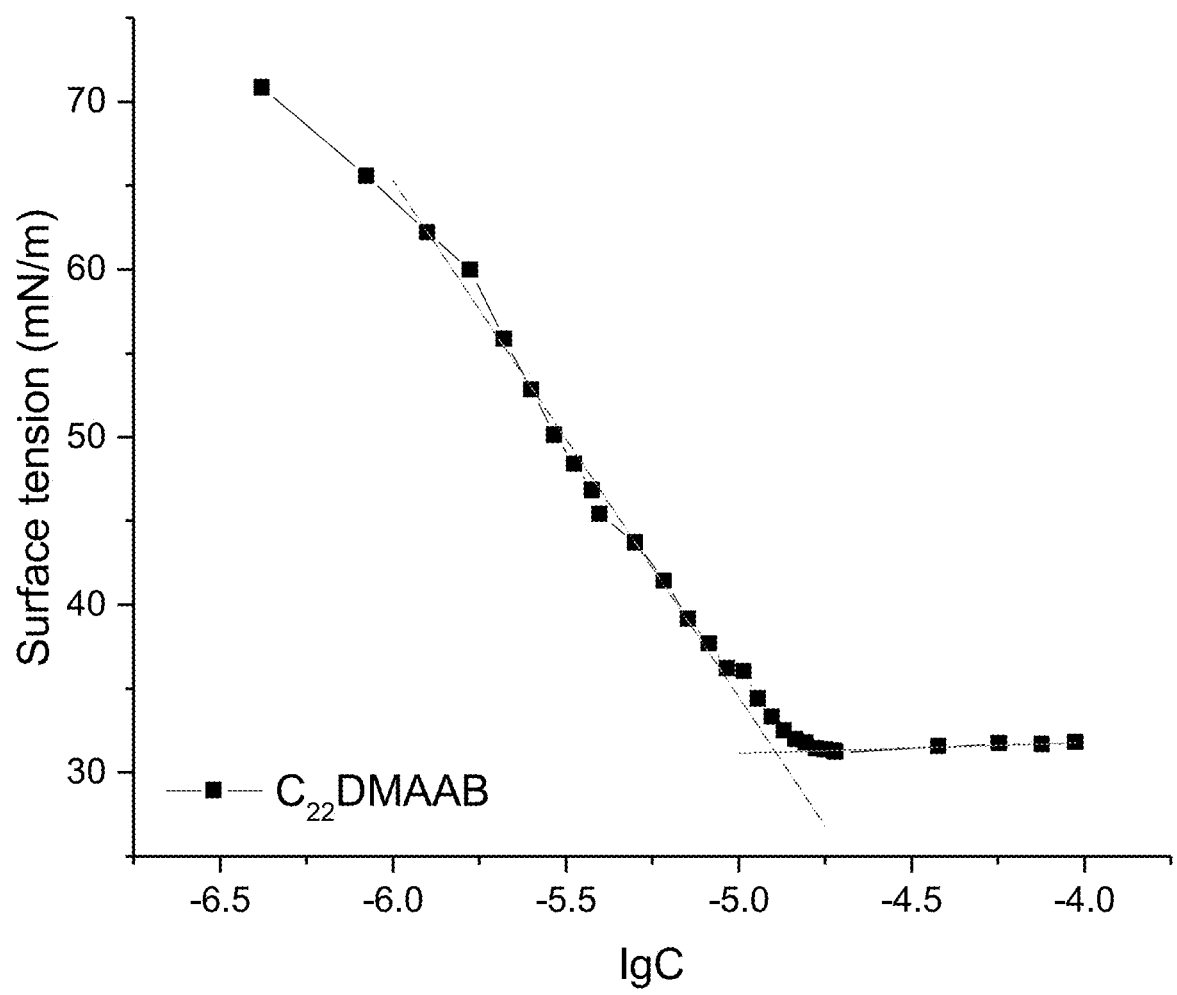
FIG. 5. shows the effect of $C_{22}$DMAAB on surface tension in seawater at 25° C.

To find the lowest surface tension with a $C_{22}DMAAB$ aqueous solution on a surface, the critical micellar concentration (CMC) was determined. During a CMC measurement, $C_{22}DMAAB$ was added to a solution to coat the surface of an object until it was fully saturated. At the point of surface saturation, called the "CMC breakpoint," the surfmer no longer attaches to the surface and begins to form micelles in solution. FIG. 5 shows the variation of surface tension as a function of $C_{22}DMAAB$ concentration; the CMC of $C_{22}DMAAB$ is calculated from the breakpoint in the curve. The surface tension at CMC ($\gamma_{cmc}$) is about 31 mN/m, the maximum surface excess concentration ($\Gamma_{max}$) is about $5.1 \times 10^{-6}$ $mol/m^2$, and the minimum area per molecule (Amin) is 0.32 nanometer squared per molecule ($nm^2$/molecule). $C_{22}DMAAB$ CMC experiments were performed at 25° C. and the results are shown in Table 1. In one or more embodiments, CMC measurements model a coating of a hard surface, such as a reservoir rock, with $C_{22}DMAAB$.

TABLE 1

| | Surface Active Properties of $C_{22}$DMAAB at 25° C. | | | | | |
|---|---|---|---|---|---|---|
| Compound | Molecular Weight (g/mol) | CMC (mg/L) | CMC (mol/L) | $\gamma_{cmc}$ (mN/in) | $\Gamma_{max}$ (mol/m$^2$) | $A_{min}$ (nm$^2$/molecule) |
| $C_{22}$DMAAB | 543.74 | 4.57 | $8.40 \times 10^{-6}$ | 31.24 | $5.14 \times 10^{-6}$ | 0.32 |

Interfacial Tension of $C_{22}$DMAAB

Figure 6:
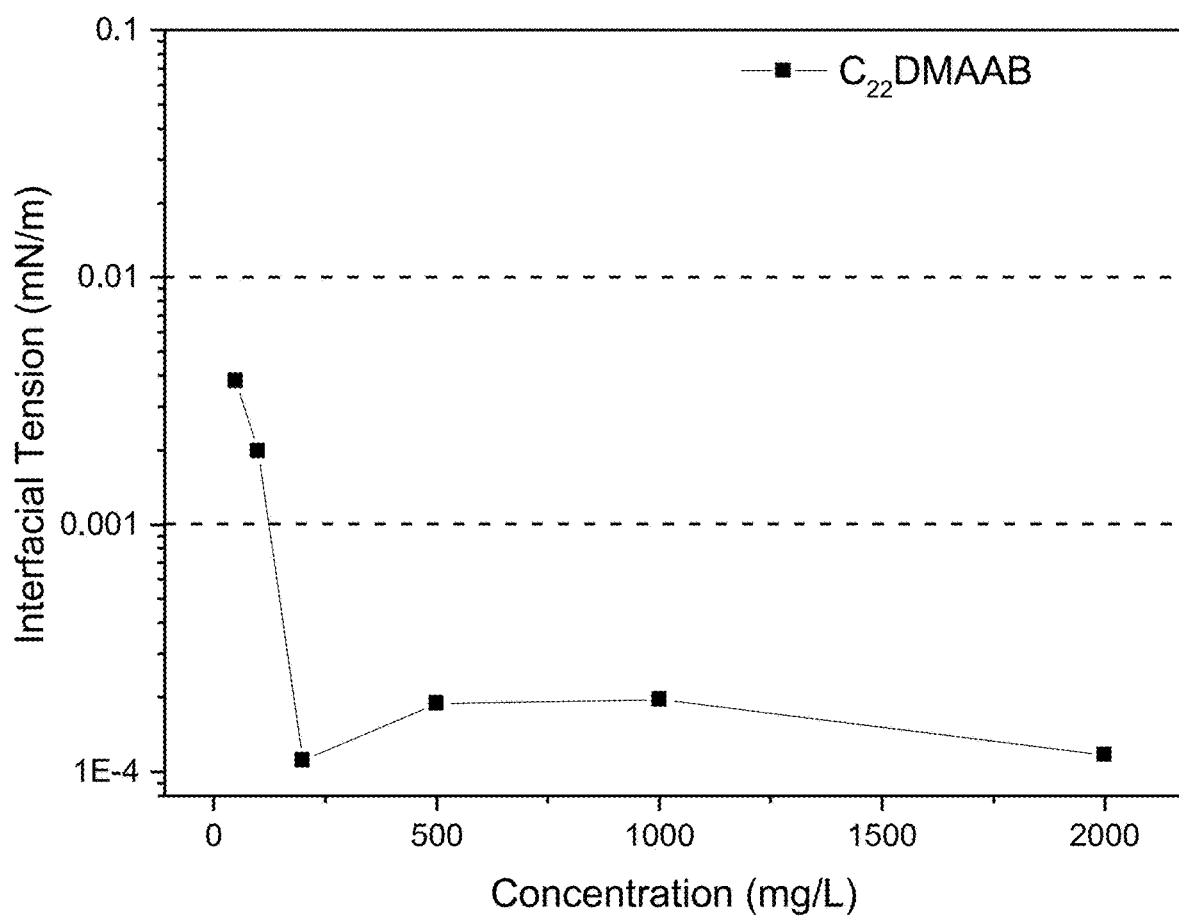
FIG. 6 shows the effect of $C_{22}$DMAAB concentration on IFT in seawater at 95° C.

Interfacial tension (IFT) was determined to find the effect of $C_{22}$DMAAB between two immiscible phases such as oil and salt water. FIG. 6 depicts results of $C_{22}$DMAAB IFT in millinewton per meter (mN/m) between crude oil and the $C_{22}$DMAAB solutions at 95° C. in seawater with a salinity of 57,670 ppm. Results of IFT studies exhibit IFT values at magnitudes of $10^4$ mN/m, for concentrations from 200 mg/L to 2000 mg/L. A low IFT value is considered effective for chemical EOR potential when the magnitude of IFT is below $10^{-2}$ mN/m. An ultra-low IFT is considered in the magnitude range of $10^{-3}$ mN/m or less. In one or more embodiments, the $C_{22}$DMAAB surfmer can be used by itself in aqueous or brine solution as a surfactant for enhanced oil recovery due to its ultra-low IFT.

A "high surface tension" may be measured from around 25 mN/m up to around 50 mN/m. Above 50 mN/m is considered very high surface tension. An example of a very high surface tension benchmark is water at 72 mN/m. Molecules with both high surface tension and very high surface tension are known to be surface active, present on the surface to an extent that the compound may modify surface properties. A maximum surface tension of $C_{22}$DMAAB in aqueous solution at critical micellar ratio is about 31 mN/m, as shown in Table 1. IFT studies result in a magnitudes of $10^4$ mN/m, shown in FIG. 6. Taken together, these data points provide a high surface tension with a low IFT. Meaning, $C_{22}$DMAAB is sufficiently surface activity to produce an effect of imbibition on a rock surface, while lowering IFT to an effective degree between oil and water for imbibition.

Solution Viscosity Vs $C_{22}$DMAAB Concentration

Figure 7:
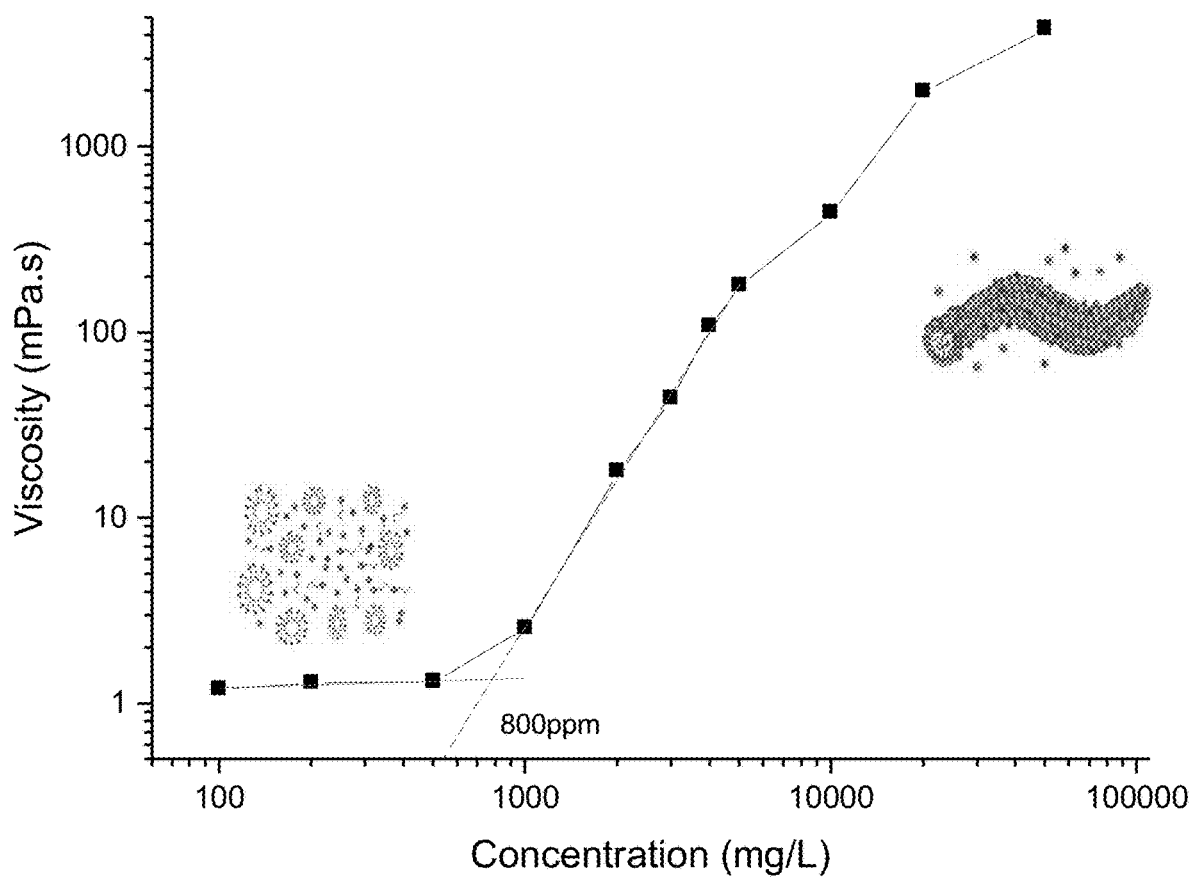
FIG. 7 shows the effect of $C_{22}$DMAAB concentration on apparent viscosity at 25° C.
Figure 8A:
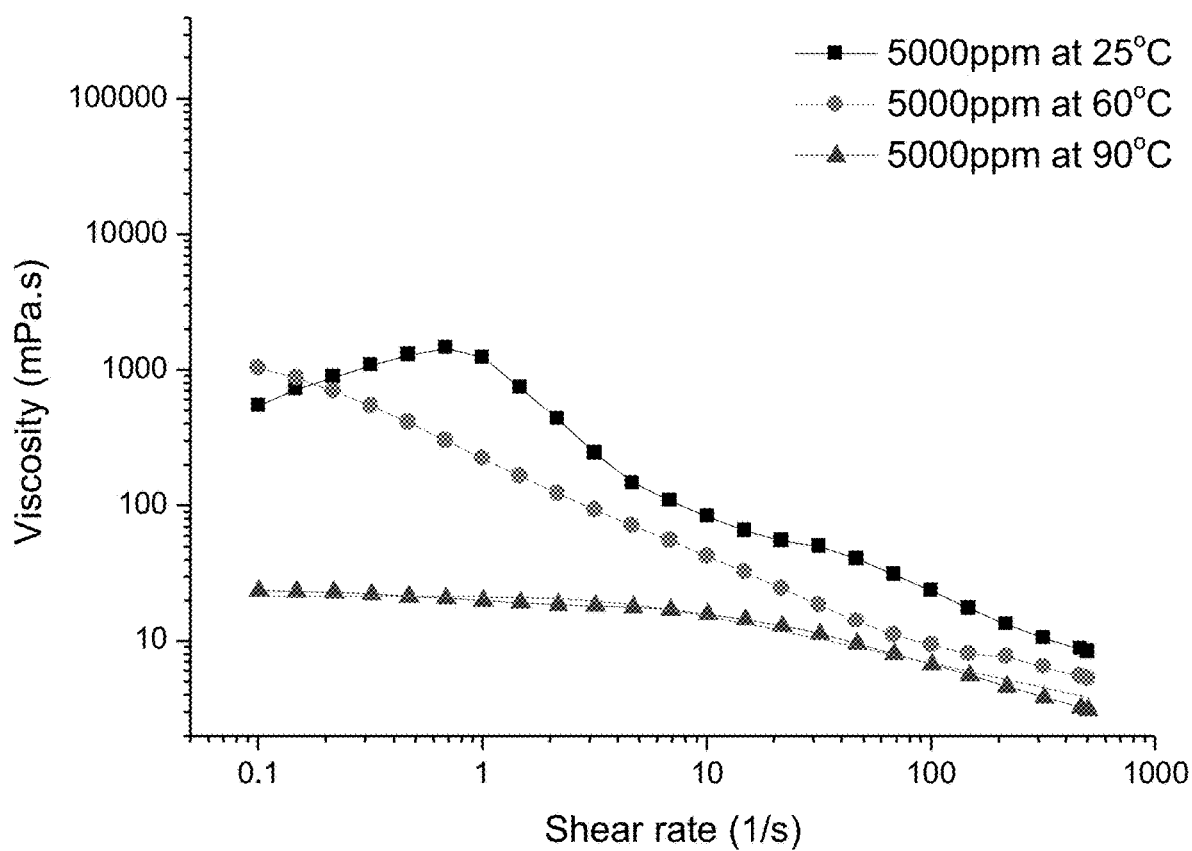
FIG. 8A depicts the effect of shear rate on the apparent viscosity of a 5,000 parts-per-million (ppm) $C_{22}$DMAAB solution at select temperatures.
Figure 8B:
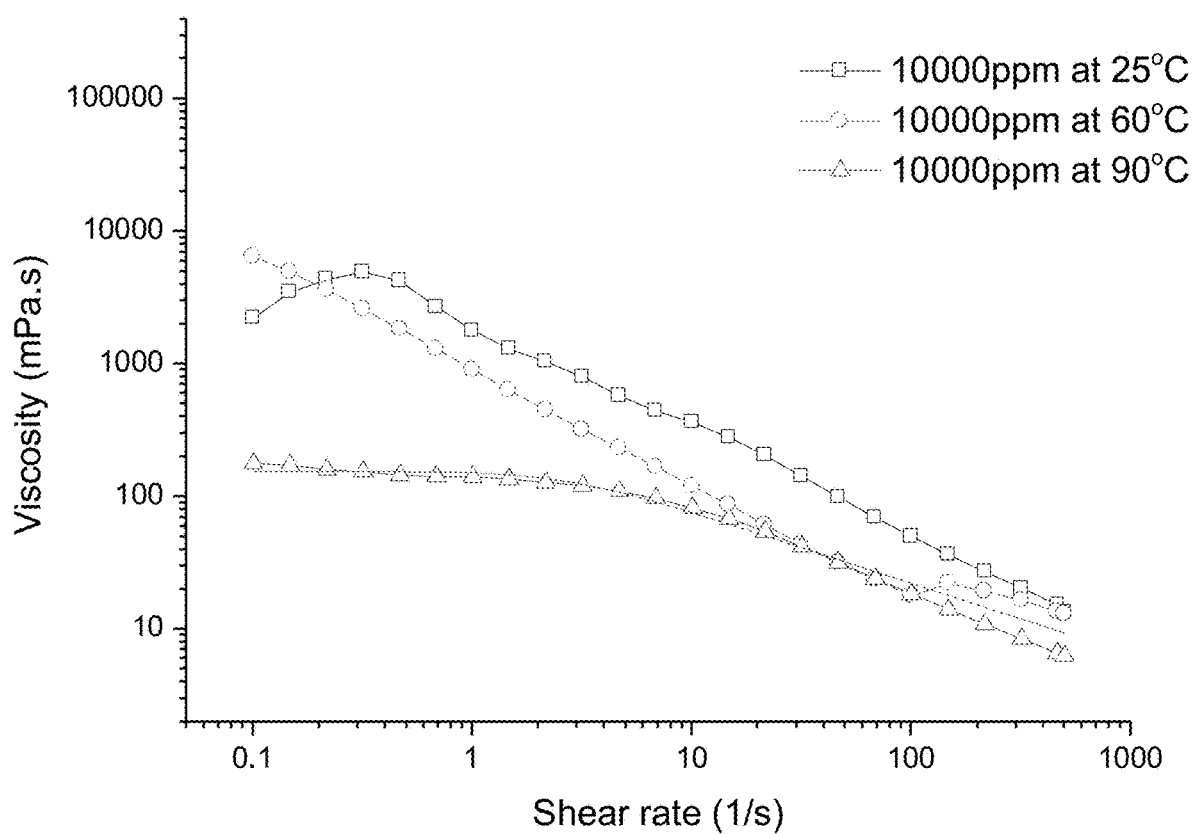
FIG. 8B depicts the effect of shear rate on the apparent viscosity of a 10,000 ppm $C_{22}$DMAAB solution at select temperatures.
Figure 8C:
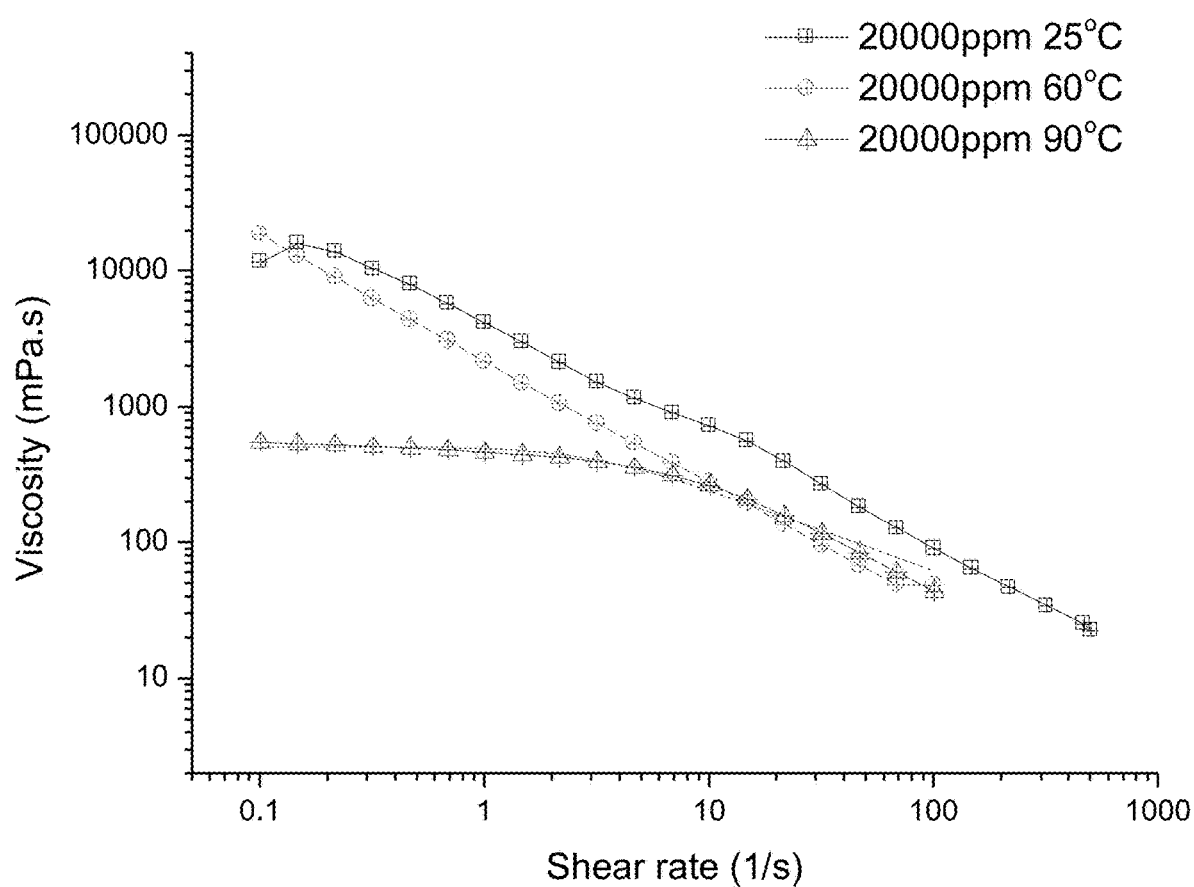
FIG. 8C depicts the effect of shear rate on the apparent viscosity of a 20,000 ppm $C_{22}$DMAAB solution at select temperatures.
Figure 8D:
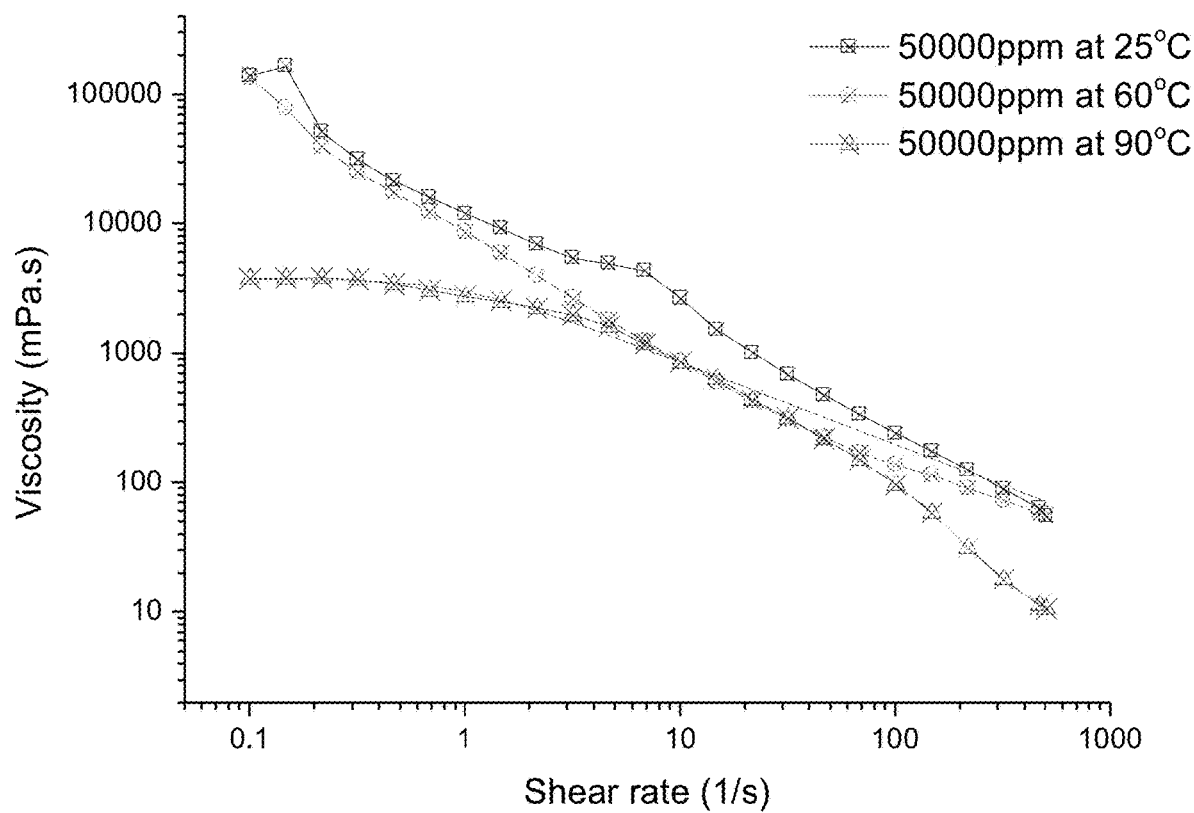
FIG. 8D depicts the effect of shear rate on the apparent viscosity of a 50,000 ppm $C_{22}$DMAAB solution at select temperatures.

The viscosity of a $C_{22}$DMAAB solution was measured using Brookfield DVIII viscometer at various concentrations, the results of which are presented in FIG. 7. The spindle #0 was selected for the measurement with a shear rate of 6 revolutions per minute (rpm) (7.34 s$^{-1}$) and the test temperature was 25° C. As shown in FIG. 7, no apparent change of viscosity occurs at concentrations under 800 mg/L, considered to be low concentration. The viscosity of a $C_{22}$DMAAB aqueous solution remains consistent at around 1 to 3 millipascal-second (mPa·s), when at a concentration less than 800 mg/L. At a concentration of 800 mg/L and above, the viscosity increases relatively linearly. A maximum tested viscosity of >1,000 mPa·s is achieved at a concentration of 100,000 mg/L. While not bound by any theory, the increase in viscosity may result in part from an intermolecular structural formation of multiple molecules of $C_{22}$DMAAB forming spherical micelles at low concentration, while inducing the formation of wormlike micelles at higher $C_{22}$DMAAB concentration. In one or more embodiments, a structural micelle formation change upon increasing concentrations contributes to higher solution viscosity. The results confirm that $C_{22}$DMAAB is a viscoelastic solution with the ability to increase viscosity, thicken under high temperature and high salinity conditions.

Shear Rate Vs. Viscosity of $C_{22}$DMAAB Solutions

The relationship between shear rate, concentration, and viscosity were also studied. The rheological properties of polymer solution were measured by a Discovery HR-2 rheometer (TA Instrument). A correlation between shear rate and the apparent viscosity of $C_{22}$DMAAB in water and brine are exhibited in FIGS. 8A-8D. $C_{22}$DMAAB illustrates a property of shear thinning behavior in seawater from concentrations of 5,000 ppm to 50,000 ppm. This shear thinning property may result from realignment of spherical micelles to wormlike micelles as shear rate (1/s) increases. However, at temperatures of 90° C. and above, $C_{22}$DMAAB has a property of low shear viscosity while also resisting shear thickening; shear viscosity is less than $4 \times 10^3$ mPa·s at high temperatures at and above 90° C. $C_{22}$DMAAB surfmer displays unexpected results of shear thickening resistance at higher temperatures. $C_{22}$DMAAB was found to have viscoelastic properties at a temperature lower than 90° C., while at higher temperatures of 90° C. and above, the $C_{22}$DMAAB solutions were determined to have a property of shear resistance in brine, as depicted in FIGS. 8A-8D. This may relate to consistency in composition and performance at higher temperatures, to an extent that the shear rate downhole remains less than about 1 s$^{-1}$ to 10 s$^{-1}$. It is known that viscosity of some solutions may decrease with increasing temperature; FIGS. 8A-8D confirm the viscosity of the samples decrease with an increase in temperature. However, $C_{22}$DMAAB exhibited a property of unexpectedly low shear viscosity of $3.79 \times 10^3$ mPa·s with 5 wt % $C_{22}$DMAAB at high temperatures of 90° C. Low shear viscosity is considered less than $5 \times 10^3$ mPa·s to $10 \times 10^3$ mPa·s.

Example 2 Copolymerization of AMPS/$C_{22}$DMAAB

Studies were performed to investigate appropriate parameters for a typical radical aqueous copolymerization according to embodiments herein. A number of polymerization reactions to form AMPS/$C_{22}$DMAAB were performed, as outlined in the tables below, to investigate appropriate conditions for producing copolymers having desirable properties of viscosity, solubility, and long-term stability suitable for CEOR operations.

In each of the copolymerization experiments, an amount of monomer was dissolved in deionized (DI) water. The mixture was stirred for about 15 min, and next an amount of $C_{22}$DMAAB was added. The reaction mixture and reaction vessel were purged with nitrogen for 30 min. The reactant was heated to reaction temperature in a tempering kettle under a nitrogen atmosphere. Initiator or an initiator mixture was then added to the solution and the polymerization proceeded at reaction temperature for a time period. The reaction product was then recovered.

In a first series of experiments, the effect of the molar ratio of AMPS to $C_{22}$DMAAB was investigated, the results of which are shown in Table 2. These results indicate that a suitable molar ratio of AMPS to $C_{22}$DMAAB may be around 100:0.1 for the reaction conditions and initiators selected.

TABLE 2

Effect of Mole Ratio of AMPS/$C_{22}$DMAAB at 40° C.

| | mole ratio | | Initiator (wt %)[a] | | Temp. | Conc. | | Time | Viscosity(mPa · s)[b] | |
|---|---|---|---|---|---|---|---|---|---|---|
| | AMPS | $C_{22}$DMAAB | KPS-NaHSO$_3$ | AIBI | (° C.) | (wt %) | pH | (hr) | 25° C. | 90° C. |
| 1 | 100 | 10 | 0 | 0.2 | 40 | 25 | 7 | 24 | — | — |
| 2 | 100 | 5 | 0 | 0.2 | 40 | 25 | 7 | 24 | — | — |
| 3 | 100 | 2 | 0 | 0.2 | 40 | 25 | 7 | 24 | — | — |
| 4 | 100 | 1 | 0 | 0.2 | 40 | 25 | 7 | 24 | — | — |
| 5 | 100 | 0.5 | 0 | 0.2 | 40 | 25 | 7 | 24 | 8.31 | 2.55 |
| 6 | 100 | 0.25 | 0 | 0.2 | 40 | 25 | 7 | 24 | 6.321 | 4.51 |
| 7 | 100 | 0.1 | 0 | 0.2 | 40 | 25 | 7 | 24 | 19.94 | 8.16 |
| 8 | 100 | 0.05 | 0 | 0.2 | 40 | 25 | 7 | 24 | 16.5 | 6.36 |

Note:
[a]Initiator: KPS-NaHSO$_3$ (weight ratio: 2/1) and AIBI feed weight percentage relative to total monomers;
[b]Copolymer concentration in sea water: 5000 mg/L, measurement condition: shear rate at 6.81 s$^{-1}$;
[c]"—" means insolubility.

At a fixed molar ratio of 100:0.1, the effect of initiator and polymerization temperature was investigated, the results of which are shown in Tables 3-5. Tables 3-5 display that the copolymer could have a highest apparent viscosity when the combination and amount of initiator is: KPS-NaHSO$_3$ 0.05 wt. %+AIBI 0.025 wt. % and the reaction temperature is about 20° C.

TABLE 3

Effect of Initiators Concentration at 40° C.

| | mole ratio | | Initiator (wt %)[a] | | Temp. | Conc. | | Time | Viscosity(mPa · s)[b] | |
|---|---|---|---|---|---|---|---|---|---|---|
| | AMPS | $C_{22}$DMAAB | KPS-NaHSO$_3$ | AIBI | (° C.) | (wt %) | pH | (hr) | 25° C. | 90° C. |
| 1 | 100 | 0.1 | 0 | 0.2 | 40 | 25 | 7 | 24 | 16.5 | 6 |
| 2 | 100 | 0.1 | 0 | 0.1 | 40 | 25 | 7 | 24 | 17 | 6.5 |
| 3 | 100 | 0.1 | 0 | 0.05 | 40 | 25 | 7 | 24 | 16.5 | 8 |
| 4 | 100 | 0.1 | 0 | 0.025 | 40 | 25 | 7 | 24 | 22 | 12 |
| 5 | 100 | 0.1 | 0 | 0.0125 | 40 | 25 | 7 | 24 | x | x |

Note:
[a]Initiator: KPS-NaHSO$_3$ (weight ratio: 2/1) and AIBI feed weight percentage relative to total monomers;
[b]Copolymer concentration in sea water: 5000 mg/L, measurement condition: 25° C., 6.81 s$^{-1}$;
[c]"x" means no polymerization.

TABLE 4

Effect of temperature

| | mole ratio | | Initiator (wt %)[a] | | Temp. | Conc. | | Time | Viscosity(mPa · s)[b] | |
|---|---|---|---|---|---|---|---|---|---|---|
| | AMPS | $C_{22}$DMAAB | KPS-NaHSO$_3$ | AIBI | (° C.) | (wt %) | pH | (hr) | 25° C. | 90° C. |
| 1 | 100 | 0.1 | 0.025 | 0.2 | 30 | 25 | 7 | 24 | 24.5 | 13 |
| 2 | 100 | 0.1 | 0.025 | 0.2 | 20 | 25 | 7 | 24 | 35.5 | 16.5 |
| 3 | 100 | 0.1 | 0.025 | 0.2 | 10 | 25 | 7 | 24 | x | x |
| 4 | 100 | 0.1 | 0.025 | 0.2 | 5 | 25 | 7 | 24 | x | x |

Note:
[a]Initiator: KPS-NaHSO$_3$ (weight ratio: 2/1) and AIBI feed weight percentage relative to total monomers;
[b]Copolymer concentration in sea water: 5000 mg/L, measurement condition: shear rate at 6.81 s$^{-1}$;
[c]"x" means no polymerization.

TABLE 5

Effect of Initiators at 20° C.

| | mole ratio | | Initiator (wt %)[a] | | Temp. | Conc. | | Time | Viscosity(mPa · s)[b] | |
|---|---|---|---|---|---|---|---|---|---|---|
| | AMPS | $C_{22}$DMAAB | KPS-NaHSO$_3$ | AIBI | (° C.) | (wt %) | pH | (hr) | 25° C. | 90° C. |
| 1 | 100 | 0.1 | 0.025 | 0.1 | 20 | 25 | 7 | 24 | 58.5 | 30.5 |
| 2 | 100 | 0.1 | 0.025 | 0.05 | 20 | 25 | 7 | 24 | 46 | 25 |

TABLE 5-continued

Effect of Initiators at 20° C.

| | mole ratio | | Initiator (wt %)[a] | | Temp. | Conc. | | Time | Viscosity(mPa·s)[b] | |
|---|---|---|---|---|---|---|---|---|---|---|
| | AMPS | C$_{22}$DMAAB | KPS-NaHSO$_3$ | AIBI | (° C.) | (wt %) | pH | (hr) | 25° C. | 90° C. |
| 3 | 100 | 0.1 | 0.025 | 0.025 | 20 | 25 | 7 | 24 | 54 | 27.5 |
| 4 | 100 | 0.1 | 0.025 | 0.0125 | 20 | 25 | 7 | 24 | 52 | 23 |
| 5 | 100 | 0.1 | 0.025 | 0 | 20 | 25 | 7 | 24 | x | x |
| 6 | 100 | 0.1 | 0.05 | 0.1 | 20 | 25 | 7 | 24 | 57 | 23.5 |
| 7 | 100 | 0.1 | 0.125 | 0.1 | 20 | 25 | 7 | 24 | 60.5 | 31.5 |
| 8 | 100 | 0.1 | 0.006 | 0.1 | 20 | 25 | 7 | 24 | x | x |
| 9 | 100 | 0.1 | 0.1 | 0.025 | 20 | 25 | 7 | 24 | 95.5 | 50 |
| 10 | 100 | 0.1 | 0.05 | 0.025 | 20 | 25 | 7 | 24 | 100 | 55.5 |
| 11 | 100 | 0.1 | 0.0125 | 0.025 | 20 | 25 | 7 | 24 | 85.5 | 42 |
| 12 | 100 | 0.1 | 0.006 | 0.025 | 20 | 25 | 7 | 24 | 91 | 40.5 |
| 13 | 100 | 0.1 | 0.0125 | 0.0125 | 20 | 25 | 7 | 24 | 66 | 28.5 |

Note:
[a]Initiator: KPS-NaHSO$_3$ (weight ratio: 2/1) and AIBI feed weight percentage relative to total monomers;
[b]Copolymer concentration in sea water: 5000 mg/L, measurement condition: shear rate at 6.81 s$^{-1}$;
[c]"x" means no polymerization.

Tables 6-8 show impacts of monomer concentration, pH value, and reaction time on the polymerization to form AMPS/C$_{22}$DMAAB. It is known in the art that a polymerization at maximum viscosity may correlate with the polymer length, the polymerization efficiency, or both. A maximum apparent viscosity of 135 mPa·s was obtained at 25° C. and 5,000 ppm of the product copolymer solution, under the conditions with a monomer concentration of 25% in water, a reaction temperature of 20° C., a pH of around 9, and a reaction time of 5 hours.

TABLE 6

Effect of monomer concentration

| | mole ratio | | Initiator (wt %)[a] | | Temp. | Conc. | | Time | Viscosity(mPa·s)[b] | |
|---|---|---|---|---|---|---|---|---|---|---|
| | AMPS | C$_{22}$DMAAB | KPS-NaHSO$_3$ | AIBI | (° C.) | (wt %) | pH | (hr) | 25° C. | 90° C. |
| 1 | 100 | 0.1 | 0.05 | 0.025 | 20 | 40 | 7 | 24 | Explosive | |
| 2 | 100 | 0.1 | 0.05 | 0.025 | 20 | 35 | 7 | 24 | polymerization | |
| 3 | 100 | 0.1 | 0.05 | 0.025 | 20 | 30 | 7 | 24 | 79 | 29 |
| 4 | 100 | 0.1 | 0.05 | 0.025 | 20 | 25 | 7 | 24 | 86.5 | 28 |
| 5 | 100 | 0.1 | 0.05 | 0.025 | 20 | 20 | 7 | 24 | 29 | 11 |
| 6 | 100 | 0.1 | 0.05 | 0.025 | 20 | 15 | 7 | 24 | 11.5 | 6 |
| 7 | 100 | 0.1 | 0.05 | 0.025 | 20 | 10 | 7 | 24 | x | x |
| 8 | 100 | 0.1 | 0.05 | 0.025 | 20 | 5 | 7 | 24 | x | x |

Note:
[a]Initiator: KPS-NaHSO$_3$ (weight ratio: 2/1) and AIBI feed weight percentage relative to total monomers;
[b]Copolymer concentration in sea water: 5000 mg/L, measurement condition: shear rate at 6.81 s$^{-1}$;
[c]"x" means no polymerization.

TABLE 7

Effect of pH value

| | mole ratio | | Initiator (wt %)[a] | | Temp. | Conc. | | Time | Viscosity(mPa·s)[b] | |
|---|---|---|---|---|---|---|---|---|---|---|
| | AMPS | C$_{22}$DMAAB | KPS-NaHSO$_3$ | AIBI | (° C.) | (wt %) | pH | (hr) | 25° C. | 90° C. |
| 1 | 100 | 0.1 | 0.05 | 0.025 | 20 | 25 | <1 | 24 | 52.5 | 22.5 |
| 2 | 100 | 0.1 | 0.05 | 0.025 | 20 | 25 | 3 | 24 | 3 | 1.5 |
| 3 | 100 | 0.1 | 0.05 | 0.025 | 20 | 25 | 5 | 24 | 5 | 2.5 |
| 4 | 100 | 0.1 | 0.05 | 0.025 | 20 | 25 | 7 | 24 | 92.5 | 46.5 |
| 5 | 100 | 0.1 | 0.05 | 0.025 | 20 | 25 | 9 | 24 | 106 | 61.18 |
| 6 | 100 | 0.1 | 0.05 | 0.025 | 20 | 25 | 11 | 24 | x | x |

Note:
[a]Initiator KPS-NaHSO$_3$ (weight ratio: 2/1) and AIBI feed weight percentage relative to total monomers:
[b]Copolymer concentration in sea water: 5000 mg/L. measurement condition: shear rate at 6.81 s$^{-1}$;
[c]"x" means no polymerization.

TABLE 8

Effect of reaction time

| | mole ratio | | Initiator (wt %)[a] | | Temp. | Conc. | | Time | Viscosity(mPa · s)[b] | |
|---|---|---|---|---|---|---|---|---|---|---|
| | AMPS | $C_{22}$DMAAB | KPS-NaHSO$_3$ | AIBI | (° C.) | (wt %) | pH | (hr) | 25° C. | 90° C. |
| 1 | 100 | 0.1 | 0.05 | 0.025 | 20 | 25 | 9 | 0.5 | 37 | 23.5 |
| 2 | 100 | 0.1 | 0.05 | 0.025 | 20 | 25 | 9 | 1 | 41.5 | 25 |
| 3 | 100 | 0.1 | 0.05 | 0.025 | 20 | 25 | 9 | 2 | 96.5 | 56.5 |
| 4 | 100 | 0.1 | 0.05 | 0.025 | 20 | 25 | 9 | 3 | 116 | 63.5 |
| 5 | 100 | 0.1 | 0.05 | 0.025 | 20 | 25 | 9 | 3 | 135 | 61.5 |
| 6 | 100 | 0.1 | 0.05 | 0.025 | 20 | 25 | 9 | 5 | 135 | 61.5 |
| 7 | 100 | 0.1 | 0.05 | 0.025 | 20 | 25 | 9 | 6 | 135 | 61.5 |
| 8 | 100 | 0.1 | 0.05 | 0.025 | 20 | 25 | 9 | 12 | 137 | 62.5 |
| 9 | 100 | 0.1 | 0.05 | 0.025 | 20 | 25 | 9 | 24 | 135 | 61.5 |

Note:
[a]Initiator: KPS-NaHSO$_3$ (weight ratio: 2/1) and AIBI feed weight percentage relative to total monomers;
[b]Copolymer concentration in sea water: 5000 mg/L, measurement condition: shear rate at 6.81 s$^{-1}$.

Based on the above results, suitable conditions of radical aqueous polymerization to form surfmer compolymers according to embodiments herein may include reactant (comonomer plus monomer) concentrations in water in the range from 20 wt % to 30 wt %, such as about 25%, a reaction temperature in the range from about 15° C. to about 25° C., such as about 20° C., a pH in the range from about 6 to about 10, such as around 9, and a reaction time of about 3-8 hours, such as about 5 hours.

Characterization of AMPS/$C_{22}$DMAAB Copolymer

Figure 9:
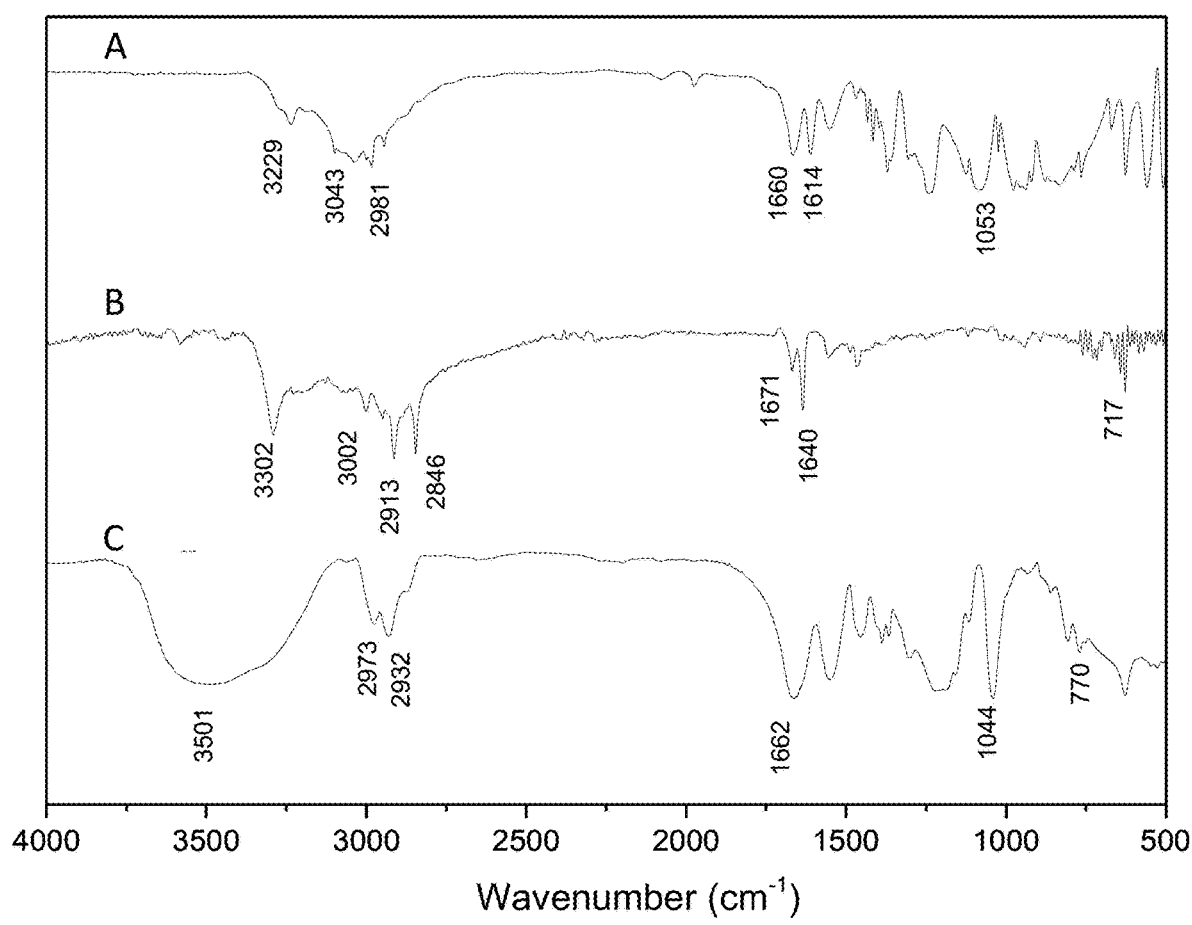
FIG. 9 compares an IR spectra of AMPS (Line A) with that of $C_{22}$DMAAB (Line B) and AMPS/$C_{22}$DMAAB (Line C).

The product AMPS/$C_{22}$DMAAB was characterized with IR spectroscopy and gel permeation chromatography (GPC). The IR spectra of AMPS, $C_{22}$DMAAB and AMPS/$C_{22}$DMAAB copolymer are compared in FIG. 9, as lines A, B, and C, respectively. The IR spectra may be used to show reaction completion and identify presence of the copolymer. IR data illustrates reaction completion from the absence of specific peaks in the starting material. The wide absorption at 3501 cm$^{-1}$ may be attributed to —N—H stretching vibrations. The peaks at 2973 cm$^{-1}$ and 2932 cm$^{-1}$ may be considered stretching vibrations of —CH$_3$ and —C—H (—CH$_2$—) groups. The peak at 1662 cm$^{-1}$ may be considered a —C=O stretching vibration. The characteristic peak of —SO$_3$Na group may be observed at 1044 cm$^{-1}$. The peak at 770 cm$^{-1}$ may confirm the alkyl chain and the polymer main chain. The peaks presented previously are also displayed in the IR of copolymer AMPS/$C_{22}$DMAAB and corresponded to the peaks of each monomer. The AMPS/$C_{22}$DMAAB copolymer indicates no remaining terminal carbon double bonds around about 1650 cm$^{-1}$ to about 1600 cm$^{-1}$. In one or more embodiments, the peaks in FIG. 9 confirm the structure of AMPS/$C_{22}$DMAAB and the absence of starting comonomer.

Gel permeation chromatography (GPC) was used to characterize properties of AMPS/$C_{22}$DMAAB, shown in Table 9. Absolute molecular weight (Mw), gyration radius (Rg), and viscosity-average molecular weight (Mv) were obtained using a viscosity detector. Hydrodynamic radius (Rh) was deduced by Einstein viscosity equation. The Mw of AMPS/$C_{22}$DMAAB obtained was around 5.73 MDa. The polydispersity index (PDI) was 1.64 and the Rg/Rh ratio was 1.17, indicating narrow molecular weight distribution.

TABLE 9

Molecular Information of Copolymer AMPS/$C_{22}$DMAAB

| Copolymer | Mw (MDa) | Mv (MDa) | Mn (MDa) | PDI | Rg (nm) | Rh (nm) | Rg/Rh |
|---|---|---|---|---|---|---|---|
| AMPS/$C_{22}$DMAAB | 5.73 | 7.50 | 3.49 | 1.64 | 107.23 | 91.36 | 1.17 |

Example 3: Copolymerization of AM/$C_{22}$DMAAB 35.54 g (or 500 mmol) monomer AM was dissolved in 107.03 g DI water in a 250 mL flask with a monomer concentration of 25 wt. %. The mixture was stirred for 15 min, and next 0.14 g (or 0.25 mmol) $C_{22}$DMAAB was added into the flask. The reaction mixture and flask was purged with nitrogen for 30 min. The reactant was heated to reaction temperature in a tempering kettle under a nitrogen atmosphere. 0.05 wt. % of AIBI initiator was added to the solution and the polymerization proceeded at 25° C. for 4 hours. The final product AM/$C_{22}$DMAAB was obtained as a transparent gel.

Example 4: Post Polymerization Hydrolysis to Synthesize AM/AANa/$C_{22}$DMAAB

The transparent gel from Example 3 was used in a post hydrolysis process. The post hydrolysis process was conducted by adding 40 g (20 wt. %) NaOH solution and keeping it at 95° C. for 2 hours. The crude product was purified by precipitation from ethanol and dried in vacuum oven at 50° C. for 48 hours. The final product AM/AANa/$C_{22}$DMAAB was obtained as a white polymer powder.

Performance of AMPS/$C_{22}$DMAAB Copolymer

The properties and performance of AMPS/$C_{22}$DMAAB copolymers according to embodiments herein was investigated as described below.

Figure 10:
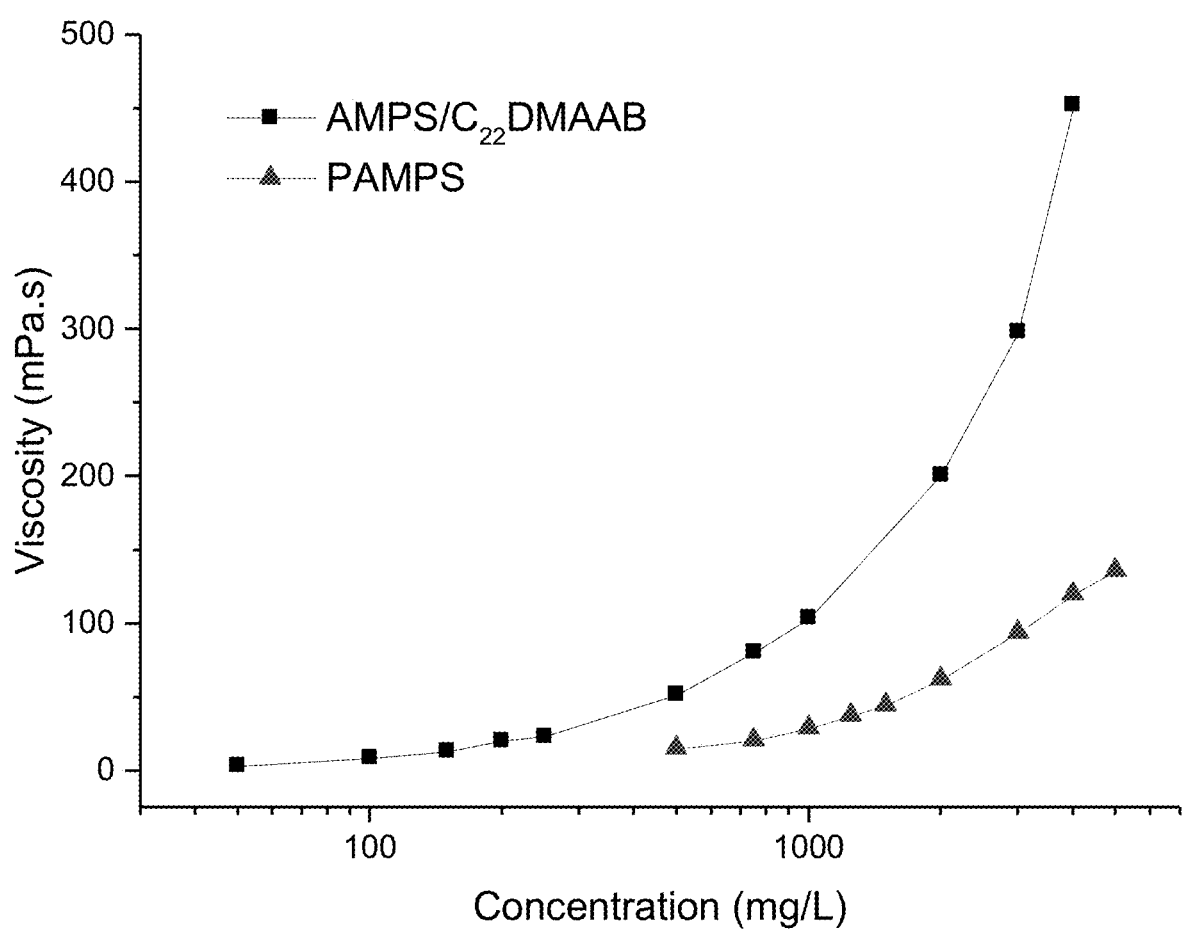
FIG. 10 depicts the effect of copolymer concentration on apparent viscosity in DI water at 25° C. for copolymers according to embodiments herein.

Effect of Copolymer Concentration on Apparent Viscosity: A relationship between polymer concentration (mg/L) and apparent viscosity (mPa·s) for copolymer AMPS/$C_{22}$DMAAB were investigated, the results of which are shown in FIG. 10. The measurements were conducted at 25° C. using Brookfield DVIII viscometer with shear rate of 6 rpm (7.34 s$^{-1}$). Results for a comparative example polymer, poly-(2-(acrylamido)-2-methylpropanesulfonic acid or PAMPS, are also shown in FIG. 10. Viscosity increases with increasing polymer concentration in each test. Further, copolymer AMPS/C$_{22}$DMAAB provides higher viscosity, greater thickening than PAMPS. Based on these results, one or more embodiments of copolymers herein, such as a copolymer of surfmer C$_{22}$DMAAB, may be used for the purpose of increasing viscosity of a solution to a greater extent than a commercially available polymer surfactant.

Figure 11:
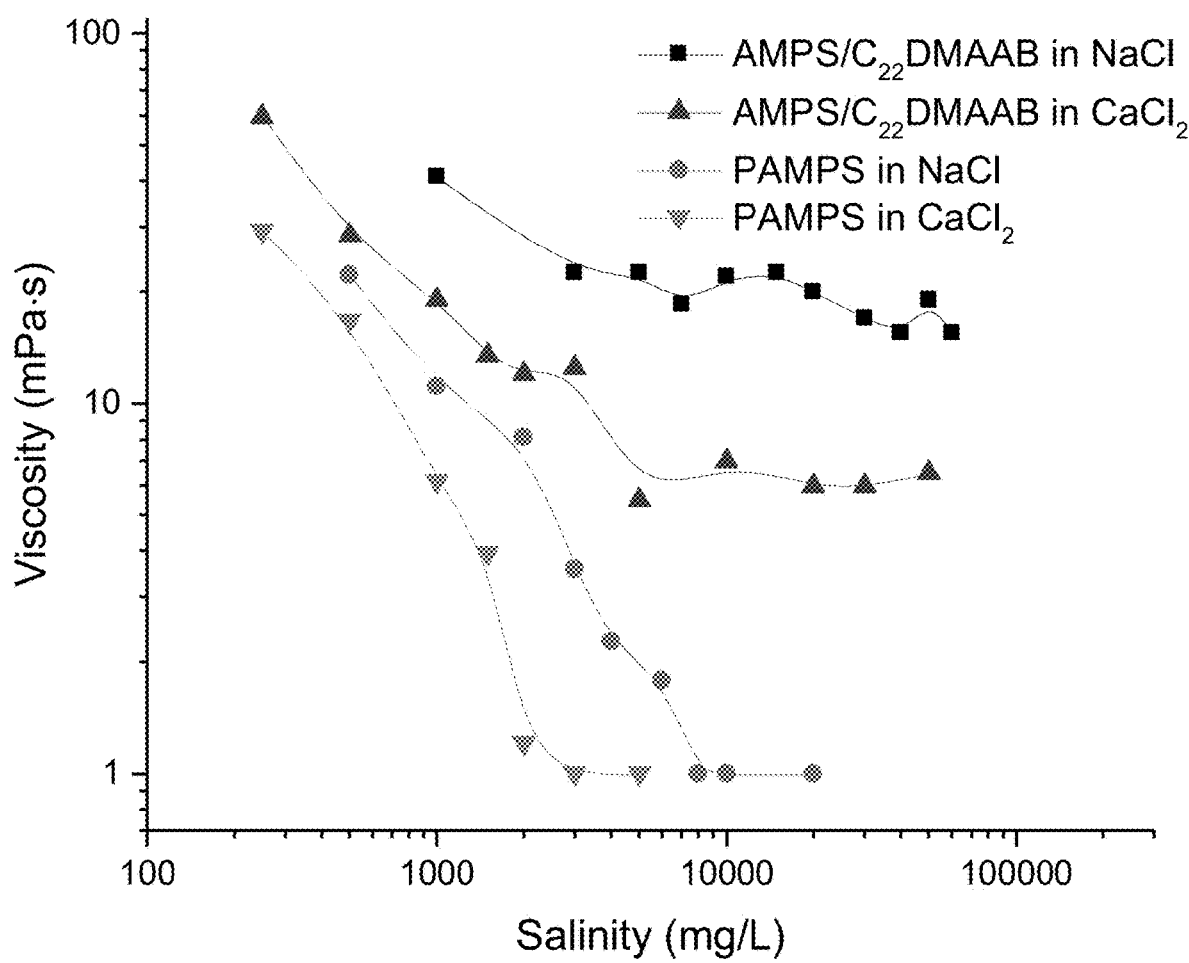
FIG. 11 depicts the effect of salinity on apparent viscosity of copolymer solutions according to embodiments herein at 25° C.

Effect of Salts on Apparent Viscosity: The apparent viscosity of a 2000 ppm copolymer solution in brine was investigated. Copolymers studied included an AMPS/C$_{22}$DMAAB copolymer as produced in Example 2 above, and a comparative PAMPS polymer. The salts used in the study included sodium chloride and calcium chloride, and the salinity was varied from 200 mg/L to 100000 mg/L. The viscosity measurements were conducted at 25° C. using Brookfield DVIII viscometer with shear rate of 6 rpm (7.34 s$^{-1}$). Viscosity versus concentration of inorganic salts are exhibited in FIG. 11. In general, viscosity (mPa·s) decreased with an increase in salinity or salt concentration (mg/L). The viscosity continued to decrease until the salt concentration reached a critical concentration. Each combination of copolymer and salt displayed a unique critical concentration point. Of the copolymers tested, AMPS/C$_{22}$DMAAB displays the least viscosity change before it reaches a critical concentration point. One effect of this property is that AMPS/C$_{22}$DMAAB remains at a higher viscosity than PAMPS after reaching a critical concentration point, in both NaCl and CaCl$_2$ solution. In other words, a copolymer surfmer of C$_{22}$DMAAB has higher salinity tolerance than PAMPS while it retains performance as a viscosity modifier, as shown in FIG. 11.

Figure 12:
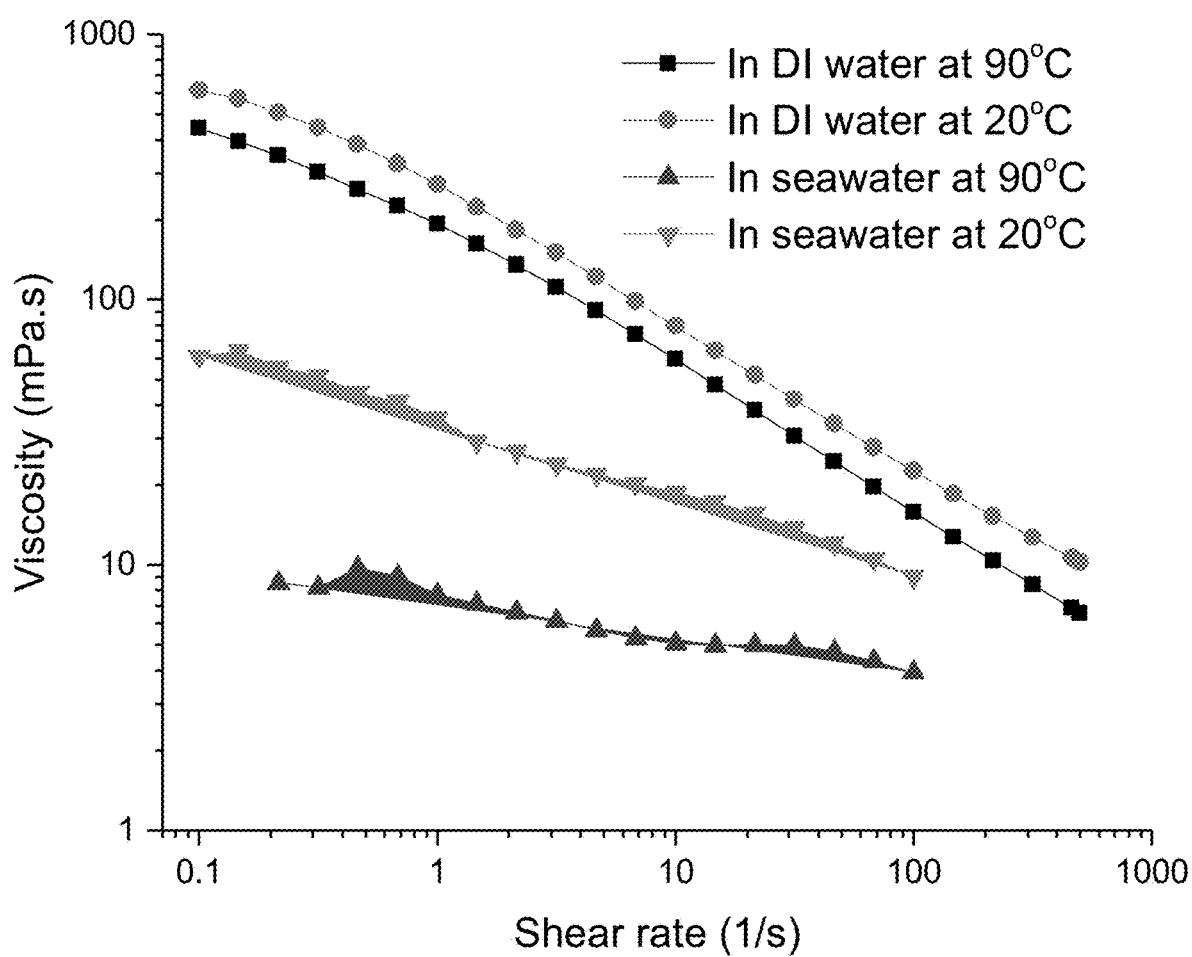
FIG. 12 shows the effect of shear rate on the apparent viscosity of copolymer AMPS/$C_{22}$DMAAB.

Effect of Shear Rates on Apparent Viscosity: The shear thinning behavior of AMPS/C$_{22}$DMAAB was investigated. The viscosity of 2000 ppm solutions of AMPS/C$_{22}$DMAAB in DI water and in seawater were investigated at both 20° C. and 90° C. The results are presented in FIG. 12. As shear rate (1/s) increased the copolymer displayed shear thinning behavior in both DI water and seawater. This behavior of shear thinning of copolymer AMPS/C$_{22}$DMAAB with increasing shear rate is similar to the C$_{22}$DMAAB monomer presented above.

Figure 13:
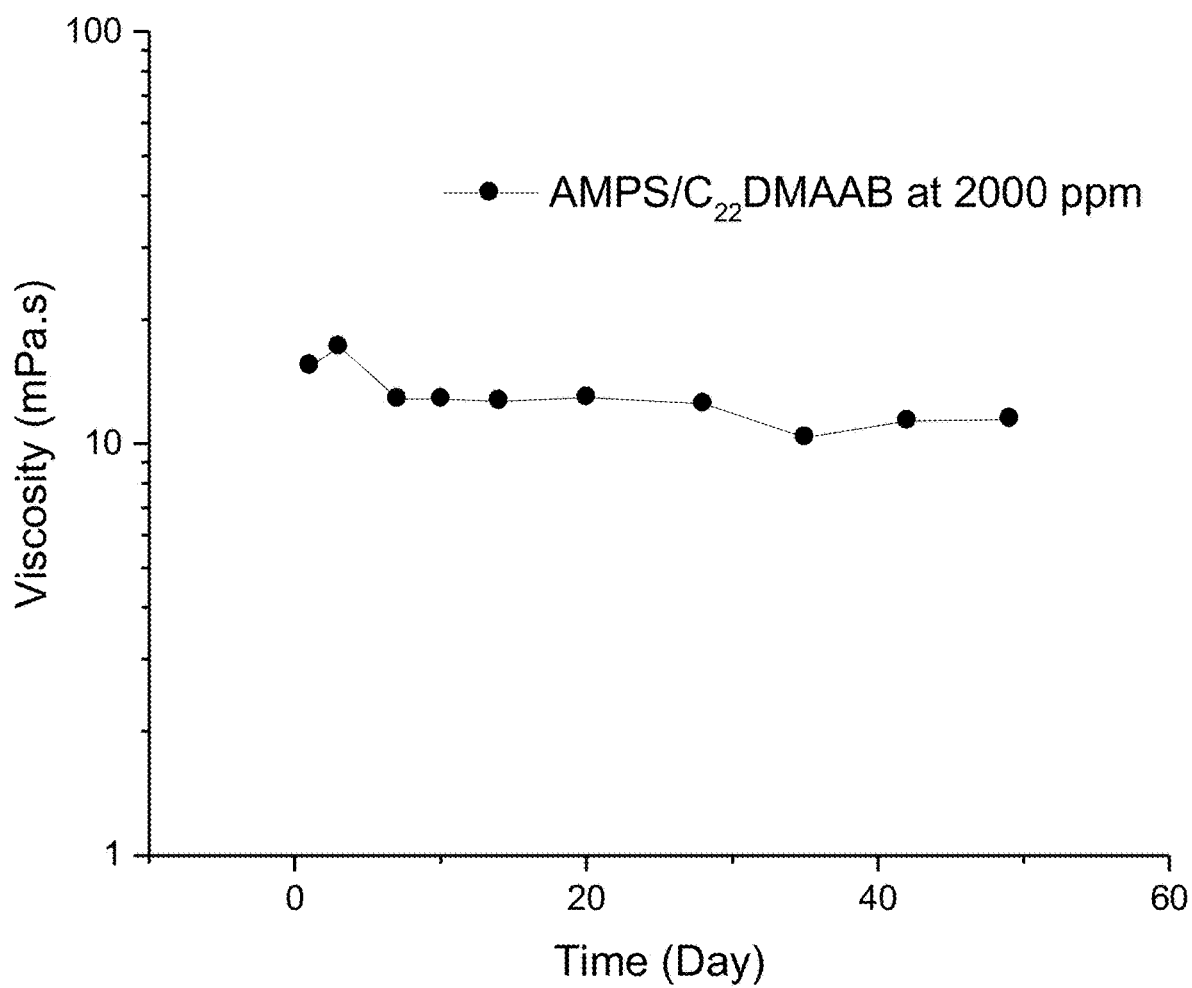
FIG. 13 shows the stability of polymers according to embodiments herein in seawater at 95° C. over a period of 50 days.

Aging Time Dependence of Polymer Viscosity: A 2000 ppm solution of copolymer AMPS/C$_{22}$DMAAB in seawater was aged at 95° C. to determine the effect of time at temperature on the performance of the copolymer. The results of the viscosity aging tests is presented in FIG. 13. As shown by the results, surfmer copolymers herein may provide a copolymer with good thermal stability and chemical stability in high salinity and high temperature conditions. Specifically, the viscosity of copolymer AMPS/C$_{22}$DMAAB in high salinity and high temperature conditions remained relatively stable from day 8 of stability testing onward. The viscosity of AMPS/C$_{22}$DMAAB is only slightly reduced after the first week, as depicted in FIG. 13. Further, no precipitation of AMPS/C$_{22}$DMAAB was observed during the testing, and the solution retains 74.29% of the original viscosity after 50 days at 95° C.

Performance of AM/AANa/C$_{22}$DMAAB

The properties and performance of AM/AANa/C$_{22}$DMAAB copolymers according to embodiments herein was investigated as described below.

Effect of Copolymer Concentration on Apparent Viscosity

Figure 14:
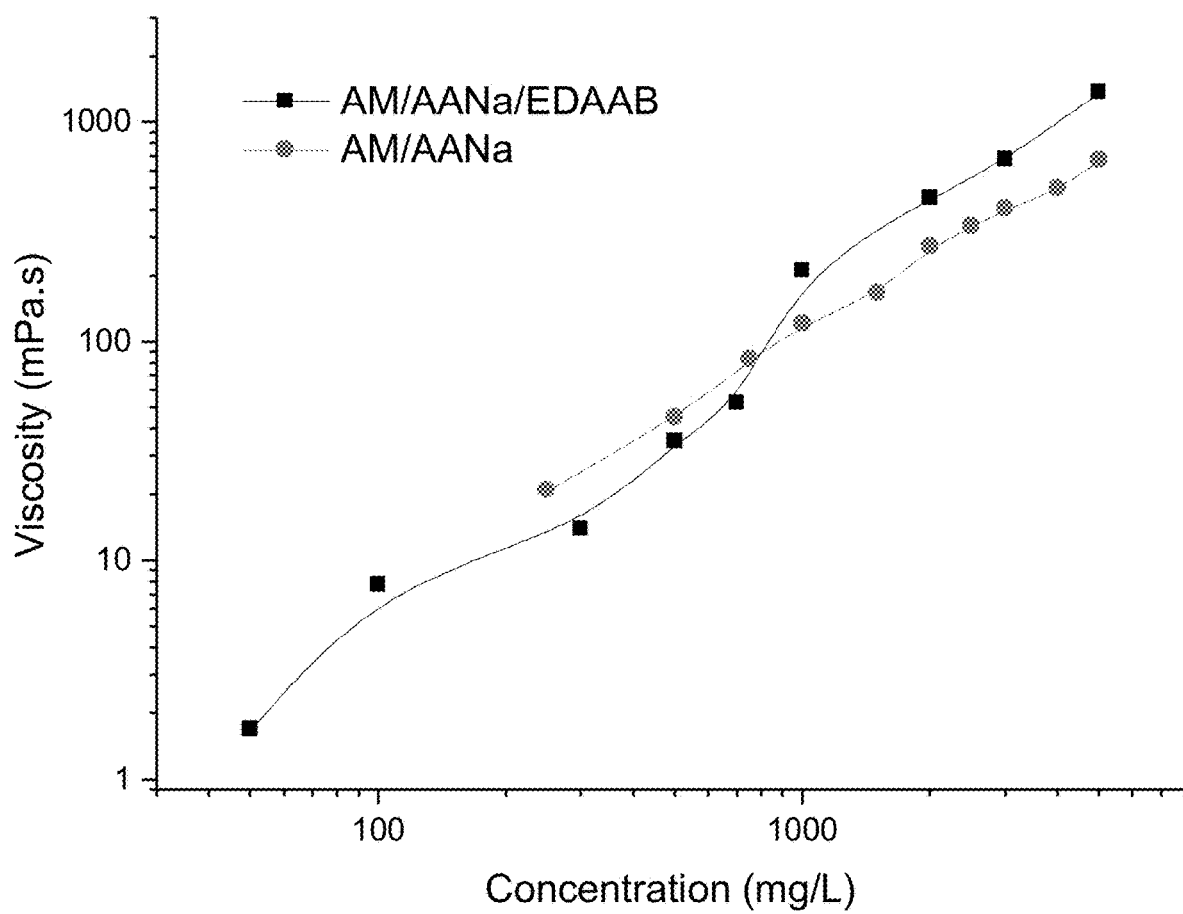
FIG. 14 shows the effect of copolymer concentration on apparent viscosity at 25° C., measured with a Brookfield DV3TLVTJ0 at a shear rate of 7.34 reciprocal seconds ($s^{-1}$) for copolymers according to embodiments herein.

Solutions of varying concentrations of the AM/AANa/C$_{22}$DMAAB copolymer as produced in Example 4 in DI water were generated. Similarly, solutions of varying concentrations of a comparative copolymer AM/AAnA (hydrolyzed polyacrylamide). The viscosity of the polymer solutions was measured using Brookfield DVIII viscometer with shear rate of 6 rpm (7.34 s$^{-1}$). The results of the tests are shown in FIG. 14, and show that the apparent viscosities increased with an increasing concentration of copolymers. However, the solution viscosity of copolymer AM/AANa/C$_{22}$DMAAB is higher than the viscosity of AM/AANa solution at concentrations above around 1000 mg/L. Compared with AM/AANa, copolymer AM/AANa/C$_{22}$DMAAB presents a greater thickening ability. This may be due in part to the small amount of C$_{22}$DMAAB groups in the side chain of the copolymer. Without being bound by any theory, the long hydrophobic tail groups can interlace with portions other molecules, such as the copolymer chain and side chains, to form a tight network.

Figure 15:
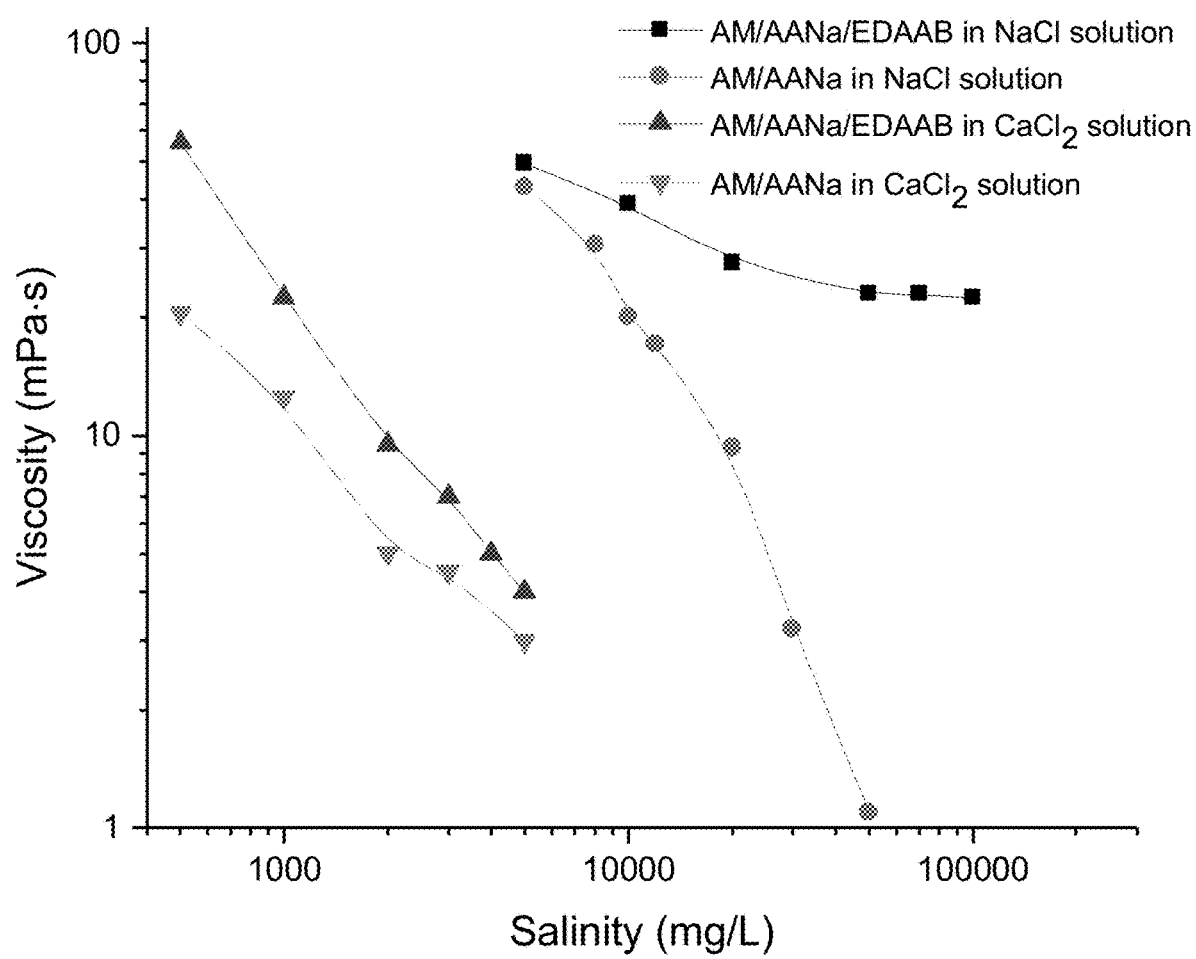
FIG. 15 shows the effect of salt concentration on apparent viscosity of copolymer solution at 25° C. for copolymers according to embodiments herein.

Salt Tolerance Effect on Apparent Viscosity: The apparent viscosity of a 2000 ppm copolymer solution in brine was investigated. Copolymers studied included an AM/AANa/C$_{22}$DMAAB copolymer as produced in Example 3 above, and a comparative AM/AANa copolymer. The salts used in the study included sodium chloride and calcium chloride, and the salinity was varied from 100 mg/L to 100000 mg/L. The viscosity measurements were conducted at 25° C. using Brookfield DVIII viscometer with shear rate of 6 rpm (7.34 s$^{-1}$). Viscosity versus concentration of inorganic salts results are exhibited in FIG. 15. The results in FIG. 15 show that the synthesized copolymers AM/AANa/C$_{22}$DMAAB remain in a range of 40-50 mPa·s in salt concentration greater than about 10,000 mg/L. At the same concentration of 10,000 mg/L, the copolymer control (AM/AANa) viscosity drops to less than 3 mPa·s. AM/AANa/C$_{22}$DMAAB also exhibits unexpectedly low viscosity decrease in the presence of some inorganic salts, such as NaCl, even at very high salt concentrations of 100,000 mg/L. The phenomenon of AM/AANa/C$_{22}$DMAAB retaining higher viscosity in the presence of highly concentrated salt solutions may be due in part to the small amount of amphiphilic groups in the side of polymer chain, which can lead to formation of a tight intramolecular and intermolecular network and enhance the salts tolerance in solution.

Based on the above results and characterizations, the surfmer C$_{22}$DMAAB performs well under harsh conditions including high temperature and high salinity environments. The copolymers synthesized from C$_{22}$DMAAB also exhibit good performance with temperature and saline resistance.

As described above, embodiments herein are directed toward surfmers and surfmer copolymers having a long hydrophobic tail. The surfmers and surfmer copolymers according to embodiments herein may have one or more properties, including interfacial tension, temperature tolerance, viscosity, and salinity tolerance, advantageous for chemical EOR operations. Based on the advantageous properties, surfmers and surfmer copolymers herein may advantageously be used in high salinity and high temperature reservoirs for chemical EOR.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A subterranean formation treatment fluid for treating a subterranean formation comprising a quaternary ammonium surfmer having the following general formula (II):

$$R^5-CH=CH-R^6-COHN-R^7-N^+R^1R^2R^4(Br^-) \quad (II)$$

where:
$R^1$ and $R^2$ are independently H or a $C_1$-$C_3$ alkyl,
$R^4$ is a $C_3$-$C_6$ alkyl having a terminal olefin double bond group,
$R^5$ is a $C_8$-$C_{16}$ alkyl,
$R^6$ is a $C_9$-$C_{16}$ alkyl, and
$R^7$ is a $C_2$-$C_6$ alkyl.

2. The subterranean formation treatment fluid for treating a subterranean formation of claim 1, wherein $R^1$ and $R^2$ are each a methyl group.

3. The subterranean formation treatment fluid for treating a subterranean formation of claim 1, wherein $R^4$ is an allyl group (—$CH_2$—CH=$CH_2$).

4. The subterranean formation treatment fluid for treating a subterranean formation of claim 1, wherein $R^5$ is a $C_8$ alkyl, $R^6$ is a $C_9$ alkyl, $R^7$ is propyl, $R^1$ and $R^2$ are each methyl, and $R^4$ is an allyl group (—$CH_2$—CH=$CH_2$) or a 1-butene group (—$CH_2$— $CH_2$—CH=$CH_2$).

5. The subterranean formation treatment fluid for treating a subterranean formation of claim 1, wherein the quaternary ammonium surfmer is a reaction product of N,N-dimethyl-erucyl-1,3-propylenediamine and allyl bromide.

6. The subterranean formation treatment fluid for treating a subterranean formation of claim 1, wherein the surfmer is in a concentration range of from 50 mg/L to 2000 mg/L of the treatment fluid.

7. A method for recovering hydrocarbons from a subterranean formation, comprising:
    injecting the subterranean formation treatment fluid comprising the quaternary ammonium surfmer of claim 1 into the subterranean formation.

* * * * *